(12) United States Patent
Stefan et al.

(10) Patent No.: US 11,237,173 B2
(45) Date of Patent: Feb. 1, 2022

(54) FULL LENGTH KINASE ACTIVITY-CONFORMATION REPORTER

(71) Applicant: UNIVERSITAT INNSBRUCK, Innsbruck (AT)

(72) Inventors: Eduard Stefan, Götzens (AT); Johanna Mayerhofer, Innsbruck (AT)

(73) Assignee: UNIVERSITAT INNSBRUCK, Innsbruck (AT)

( * ) Notice: Subject to any disclaimer, the term of this patent is extended or adjusted under 35 U.S.C. 154(b) by 0 days.

(21) Appl. No.: 16/337,217

(22) PCT Filed: Sep. 29, 2017

(86) PCT No.: PCT/EP2017/074761
§ 371 (c)(1),
(2) Date: Mar. 27, 2019

(87) PCT Pub. No.: WO2018/060415
PCT Pub. Date: Apr. 5, 2018

(65) Prior Publication Data
US 2020/0033355 A1  Jan. 30, 2020

(30) Foreign Application Priority Data
Sep. 29, 2016  (EP) .................................. 16191530

(51) Int. Cl.
*G01N 33/68* (2006.01)
(52) U.S. Cl.
CPC ..... *G01N 33/6845* (2013.01); *G01N 2333/71* (2013.01); *G01N 2500/10* (2013.01)
(58) Field of Classification Search
CPC ........... G01N 33/6845; G01N 2333/71; G01N 2500/10; C12N 15/1086; C12N 15/1055; C12N 15/10; C12Q 1/66
See application file for complete search history.

(56) References Cited

U.S. PATENT DOCUMENTS

2009/0044286 A1   2/2009  Gambhir et al.

FOREIGN PATENT DOCUMENTS

| WO | 01/94617 | 12/2001 |
|---|---|---|
| WO | 2006/039367 | 4/2006 |
| WO | 2011009218 | 1/2011 |
| WO | 2014/176700 | 11/2014 |
| WO | 2015/023433 | 2/2015 |
| WO | 2016/115376 | 7/2016 |

OTHER PUBLICATIONS

Luker et al. Luciferase Protein Complementation Assays for Bioluminescence Imaging of Cells and Mice. Methods Mol Biol. 2011; 680: 29-43.*

Michnick et al. Chemical genetic strategies to delineate MAP kinase signaling pathways using protein-fragment complementation assays (PCA). Methods 40 (2006): 287-293.*

Remy I et al.: "A cDNA library functional screening strategy based on fluorescent protein complementation assays to identify novel components of signaling pathways", MET, Academic Press, US, vol. 32, No. 4, Apr. 1, 2004 (Arp. 1, 2004), pp. 381-388.

Adelmann, et al., "Comparative profiles of BRAF inhibitors: the paradox index as a predictor of clinical toxicity", impactjournals.com/oncotarget, Oncotarget, vol. 7, No. 21, Mar. 25, 2016.

Caunt, et al., "MEK1 and MEK2 inhibitors and cancer therapy: the long and winding road", Nature Reviews, vol. 15, Oct. 2015.

Davies, et al., Mutations of the BRAF gene in human cancer, by Davies et al. (Nature 2002; 417: 949-54), Aug. 14, 2012.

Desideri, et al., "Alike but Different: RAF Paralogs and Their Signaling Outputs", Leading Edge Minireview, Cell 161, May 21, 2015.

Fleuren, et al., "The kinome 'at large' in cancer", Nature Reviews, vol. 16, Feb. 2016.

Girotti, et al., "No longer an untreatable disease: How targeted and immunotherapies have changed the management of melanoma patients", Molecular Oncology 8 (2014), Aug. 2014.

Knighton, et al., "Crystal Structure of the Catalytic Subunit of Cyclic Adenosine Monophosphate-Dependent Protein Kinase", Research Articles, Jul. 26, 1991, downloaded from www.sciencemag.org on Oct. 6, 2012, Science, Vo. 253.

Lavoie, et al., Regulation of RAF protein kinases in ERK signaling, Nature Reviews Molecular Cell Biology, vol. 16, May 2015.

Lito, et al., "Tumor adaptation and resistance to RAF inhibitors", Targeted Cancer Therapies Nature Medicine, vol. 19 No. 11, Nov. 2013.

Michnick, et al., "Universal strategies in research and drug discovery based on protein-fragment complementation assays", Nature Reviews Drug Discovery, vol. 6, Jul. 2007.

Remy, et al., "Clonal Selection and in vivo quantitation of protein interactions with protein-fragment complementation assays", Proc. Natl. Acad. Sci, USA, vol. 96, pp. 5394-5399, May 1999.

Remy, et al., "A highly sensitive protein-protein interaction assay based on Gaussia luciferase", Nature Methods, vol. 3 No. 12, Dec. 2006.

Robert, et al., "Improved Overall Survival in Melanoma with Combined Dabrafenib and Trametinib", The New England Journal of Medicine, 372;1, Jan. 1, 2015.

(Continued)

*Primary Examiner* — Iqbal H Chowdhury
(74) *Attorney, Agent, or Firm* — Workman Nydegger

(57) ABSTRACT

The present invention provides a reporter for a protein fragment complementation assay characterized in that the reporter is a fused protein comprising a first fragment, a second fragment and a protein kinase sequence section, wherein the first fragment and the second fragment are derived from different sections of the same split protein, and wherein the protein kinase sequence section intervenes between the first fragment and the second fragment and wherein the kinase sequence section comprises a kinase domain sequence and one or more regulatory sequence(s). Further the invention provides polynucleotides and cells encoding for the reporter as well as methods of conducting a protein fragment complementation assay with the reporter according to the invention.

18 Claims, 9 Drawing Sheets
Specification includes a Sequence Listing.

(56) References Cited

OTHER PUBLICATIONS

Rock, et al., "in-vivo detection of binary PKA network interactions upon activation of endogenous GPCRs", Scientific Reports, Jun. 23, 2015.

Stefan, et al., "Quantification of dynamic protein complexes using Renilla luciferase fragment complementation applied to protein kinase A activities in vivo", PNAS, vol. 104 No. 43, Oct. 23, 2007.

Zhang, et al., "RAF inhibitors that evade paradoxical MAPK pathway activation", Nature, vol. 526, Oct. 22, 2015.

Enzler, Florian, et al., "KinCon: Cell-based recording of full-length kinase conformations", wileyonlinelibrary.com/journal/iub, IUBMB Life, 2020; 72:1168-1174, Accepted Jan. 16, 2020.

* cited by examiner

SEQUENCE LISTING

```
<160> NUMBER OF SEQ ID NOS: 34

<210> SEQ ID NO 1
<211> LENGTH: 608
<212> TYPE: PRT
<213> ORGANISM: Homo sapiens

<400> SEQUENCE: 1

Met Glu Pro Pro Arg Gly Pro Pro Ala Asn Gly Ala Glu Pro Ser Arg
1               5                   10                  15

Ala Val Gly Thr Val Lys Val Tyr Leu Pro Asn Lys Gln Arg Thr Val
            20                  25                  30

Val Thr Val Arg Asp Gly Met Ser Val Tyr Asp Ser Leu Asp Lys Ala
        35                  40                  45
```

```
Leu Lys Val Arg Gly Leu Asn Gln Asp Cys Cys Val Val Tyr Arg Leu
 50                  55                  60

Ile Lys Gly Arg Lys Thr Val Thr Ala Trp Asp Thr Ala Ile Ala Pro
 65                  70                  75                  80

Leu Asp Gly Glu Glu Leu Ile Val Glu Val Leu Glu Asp Val Pro Leu
                 85                  90                  95

Thr Met His Asn Phe Val Arg Lys Thr Phe Phe Ser Leu Ala Phe Cys
            100                 105                 110

Asp Phe Cys Leu Lys Phe Leu Phe His Gly Phe Arg Cys Gln Thr Cys
        115                 120                 125

Gly Tyr Lys Phe His Gln His Cys Ser Ser Lys Val Pro Thr Val Cys
    130                 135                 140

Val Asp Met Ser Thr Asn Arg Gln Gln Phe Tyr His Ser Val Gln Asp
145                 150                 155                 160

Leu Ser Gly Gly Ser Arg Gln His Glu Ala Pro Ser Asn Arg Pro Leu
                165                 170                 175

Asn Glu Leu Leu Thr Pro Gln Gly Pro Ser Pro Arg Thr Gln His Cys
            180                 185                 190

Asp Pro Glu His Phe Pro Phe Pro Ala Pro Ala Asn Ala Pro Leu Gln
        195                 200                 205

Arg Ile Arg Ser Thr Ser Thr Pro Asn Val His Met Val Ser Thr Thr
    210                 215                 220

Ala Pro Met Asp Ser Asn Leu Ile Gln Leu Thr Gly Gln Ser Phe Ser
225                 230                 235                 240

Thr Asp Ala Ala Gly Ser Arg Gly Gly Ser Asp Gly Thr Pro Arg Gly
                245                 250                 255

Ser Pro Ser Pro Ala Ser Val Ser Ser Gly Arg Lys Ser Pro His Ser
            260                 265                 270

Lys Ser Pro Ala Glu Gln Arg Glu Arg Lys Ser Leu Ala Asp Asp Lys
        275                 280                 285

Lys Lys Val Lys Asn Leu Gly Tyr Arg Asp Ser Gly Tyr Tyr Trp Glu
    290                 295                 300

Val Pro Pro Ser Glu Val Gln Leu Leu Lys Arg Ile Gly Thr Gly Ser
305                 310                 315                 320

Phe Gly Thr Val Phe Arg Gly Arg Trp His Gly Asp Val Ala Val Lys
                325                 330                 335

Val Leu Lys Val Ser Gln Pro Thr Ala Glu Gln Ala Gln Ala Phe Lys
            340                 345                 350

Asn Glu Met Gln Val Leu Arg Lys Thr Arg His Val Asn Ile Leu Leu
        355                 360                 365

Phe Met Gly Phe Met Thr Arg Pro Gly Phe Ala Ile Ile Thr Gln Trp
    370                 375                 380

Cys Glu Gly Ser Ser Leu Tyr His His Leu His Val Ala Asp Thr Arg
385                 390                 395                 400

Phe Asp Met Val Gln Leu Ile Asp Val Ala Arg Gln Thr Ala Gln Gly
                405                 410                 415

Met Asp Tyr Leu His Ala Lys Asn Ile Ile His Arg Asp Leu Lys Ser
            420                 425                 430

Asn Asn Ile Phe Leu His Glu Gly Leu Thr Val Lys Ile Gly Asp Phe
        435                 440                 445

Gly Leu Ala Thr Val Lys Thr Arg Trp Ser Gly Ala Gln Pro Leu Glu
    450                 455                 460

Gln Pro Ser Gly Ser Val Leu Trp Met Ala Ala Glu Val Ile Arg Met
```

```
            465                 470                 475                 480

Gln Asp Pro Asn Pro Tyr Ser Phe Gln Ser Asp Val Tyr Ala Tyr Gly
                    485                 490                 495

Val Val Leu Tyr Glu Leu Met Thr Gly Ser Leu Pro Tyr Ser His Ile
                500                 505                 510

Gly Cys Arg Asp Gln Ile Ile Phe Met Val Gly Arg Gly Tyr Leu Ser
                515                 520                 525

Pro Asp Leu Ser Lys Ile Ser Ser Asn Cys Pro Lys Ala Met Arg Arg
            530                 535                 540

Leu Leu Ser Asp Cys Leu Lys Phe Gln Arg Glu Glu Arg Pro Leu Phe
545                 550                 555                 560

Pro Gln Ile Leu Ala Thr Ile Glu Leu Leu Gln Arg Ser Leu Pro Lys
                    565                 570                 575

Ile Glu Arg Ser Ala Ser Glu Pro Ser Leu His Arg Thr Gln Ala Asp
                580                 585                 590

Glu Leu Pro Ala Cys Leu Leu Ser Ala Ala Arg Leu Val Pro Ile Asp
                595                 600                 605

<210> SEQ ID NO 2
<211> LENGTH: 768
<212> TYPE: PRT
<213> ORGANISM: Homo sapiens

<400> SEQUENCE: 2

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240
```

```
Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
```

```
                    660                 665                 670
Tyr Leu Ser Pro Asp Leu Ser Lys Val Arg Ser Asn Cys Pro Lys Ala
                675                 680                 685

Met Lys Arg Leu Met Ala Glu Cys Leu Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
                740                 745                 750

Thr Pro Ile Gln Ala Gly Gly Tyr Gly Ala Phe Pro Val His Ile Asp
                755                 760                 765

<210> SEQ ID NO 3
<211> LENGTH: 650
<212> TYPE: PRT
<213> ORGANISM: Homo sapiens

<400> SEQUENCE: 3

Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
                20                  25                  30

Val Gln Gln Phe Gly Tyr Gln Arg Arg Ala Ser Asp Asp Gly Lys Leu
            35                  40                  45

Thr Asp Pro Ser Lys Thr Ser Asn Thr Ile Arg Val Phe Leu Pro Asn
50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
            100                 105                 110

Asp Trp Asn Thr Asp Ala Ala Ser Leu Ile Gly Glu Glu Leu Gln Val
        115                 120                 125

Asp Phe Leu Asp His Val Pro Leu Thr Thr His Asn Phe Ala Arg Lys
130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu Pro Val
            260                 265                 270
```

Asp Ser Arg Met Ile Glu Asp Ala Ile Arg Ser His Ser Glu Ser Ala
            275                 280                 285

Ser Pro Ser Ala Leu Ser Ser Pro Asn Asn Leu Ser Pro Thr Gly
    290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Ala Ser Glu Val Met Leu Ser
            340                 345                 350

Thr Arg Ile Gly Ser Gly Ser Phe Gly Thr Val Tyr Lys Gly Lys Trp
            355                 360                 365

His Gly Asp Val Ala Val Lys Ile Leu Lys Val Val Asp Pro Thr Pro
    370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
            420                 425                 430

Leu His Val Gln Glu Thr Lys Phe Gln Met Phe Gln Leu Ile Asp Ile
    435                 440                 445

Ala Arg Gln Thr Ala Gln Gly Met Asp Tyr Leu His Ala Lys Asn Ile
450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
            500                 505                 510

Ala Pro Glu Val Ile Arg Met Gln Asp Asn Pro Phe Ser Phe Gln
    515                 520                 525

Ser Asp Val Tyr Ser Tyr Gly Ile Val Leu Tyr Glu Leu Met Thr Gly
530                 535                 540

Glu Leu Pro Tyr Ser His Ile Asn Asn Arg Asp Gln Ile Ile Phe Met
545                 550                 555                 560

Val Gly Arg Gly Tyr Ala Ser Pro Asp Leu Ser Lys Leu Tyr Lys Asn
                565                 570                 575

Cys Pro Lys Ala Met Lys Arg Leu Val Ala Asp Cys Val Lys Lys Val
            580                 585                 590

Lys Glu Glu Arg Pro Leu Phe Pro Gln Ile Leu Ser Ser Ile Glu Leu
    595                 600                 605

Leu Gln His Ser Leu Pro Lys Ile Asn Arg Ser Ala Ser Glu Pro Ser
610                 615                 620

Leu His Arg Ala Ala His Thr Glu Asp Ile Asn Ala Cys Thr Leu Thr
625                 630                 635                 640

Thr Ser Pro Arg Leu Pro Val Phe Ile Asp
                645                 650

<210> SEQ ID NO 4
<211> LENGTH: 608
<212> TYPE: PRT
<213> ORGANISM: Homo sapiens

<400> SEQUENCE: 4

```
Met Glu Pro Pro Arg Gly Pro Pro Ala Asn Gly Ala Glu Pro Ser Arg
1               5                   10                  15

Ala Val Gly Thr Val Lys Val Tyr Leu Pro Asn Lys Gln Arg Thr Val
            20                  25                  30

Val Thr Val Arg Asp Gly Met Ser Val Tyr Asp Ser Leu Asp Lys Ala
        35                  40                  45

Leu Lys Val Arg Gly Leu Asn Gln Asp Cys Cys Val Val Tyr Arg Leu
    50                  55                  60

Ile Lys Gly Arg Lys Thr Val Thr Ala Trp Asp Thr Ala Ile Ala Pro
65                  70                  75                  80

Leu Asp Gly Glu Glu Leu Ile Val Glu Val Leu Glu Asp Val Pro Leu
                85                  90                  95

Thr Met His Asn Phe Val Arg Lys Thr Phe Phe Ser Leu Ala Phe Cys
                100                 105                 110

Asp Phe Cys Leu Lys Phe Leu Phe His Gly Phe Arg Cys Gln Thr Cys
            115                 120                 125

Gly Tyr Lys Phe His Gln His Cys Ser Ser Lys Val Pro Thr Val Cys
        130                 135                 140

Val Asp Met Ser Thr Asn Arg Gln Gln Phe Tyr His Ser Val Gln Asp
145                 150                 155                 160

Leu Ser Gly Gly Ser Arg Gln His Glu Ala Pro Ser Asn Arg Pro Leu
                165                 170                 175

Asn Glu Leu Leu Thr Pro Gln Gly Pro Ser Pro Arg Thr Gln His Cys
                180                 185                 190

Asp Pro Glu His Phe Pro Phe Pro Ala Pro Ala Asn Ala Pro Leu Gln
            195                 200                 205

Arg Ile Arg Ser Thr Cys Thr Pro Asn Val His Met Val Ser Thr Thr
        210                 215                 220

Ala Pro Met Asp Ser Asn Leu Ile Gln Leu Thr Gly Gln Ser Phe Ser
225                 230                 235                 240

Thr Asp Ala Ala Gly Ser Arg Gly Gly Ser Asp Gly Thr Pro Arg Gly
            245                 250                 255

Ser Pro Ser Pro Ala Ser Val Ser Ser Gly Arg Lys Ser Pro His Ser
            260                 265                 270

Lys Ser Pro Ala Glu Gln Arg Glu Arg Lys Ser Leu Ala Asp Asp Lys
        275                 280                 285

Lys Lys Val Lys Asn Leu Gly Tyr Arg Asp Ser Gly Tyr Tyr Trp Glu
        290                 295                 300

Val Pro Pro Ser Glu Val Gln Leu Leu Lys Arg Ile Gly Thr Gly Ser
305                 310                 315                 320

Phe Gly Thr Val Phe Arg Gly Arg Trp His Gly Asp Val Ala Val Lys
            325                 330                 335

Val Leu Lys Val Ser Gln Pro Thr Ala Glu Gln Ala Gln Ala Phe Lys
        340                 345                 350

Asn Glu Met Gln Val Leu Arg Lys Thr Arg His Val Asn Ile Leu Leu
        355                 360                 365

Phe Met Gly Phe Met Thr Arg Pro Gly Phe Ala Ile Ile Thr Gln Trp
370                 375                 380

Cys Glu Gly Ser Ser Leu Tyr His His Leu His Val Ala Asp Thr Arg
385                 390                 395                 400

Phe Asp Met Val Gln Leu Ile Asp Val Ala Arg Gln Thr Ala Gln Gly
            405                 410                 415
```

```
Met Asp Tyr Leu His Ala Lys Asn Ile Ile His Arg Asp Leu Lys Ser
            420                 425                 430

Asn Asn Ile Phe Leu His Glu Gly Leu Thr Val Lys Ile Gly Asp Phe
                435                 440                 445

Gly Leu Ala Thr Val Lys Thr Arg Trp Ser Gly Ala Gln Pro Leu Glu
    450                 455                 460

Gln Pro Ser Gly Ser Val Leu Trp Met Ala Ala Glu Val Ile Arg Met
465                 470                 475                 480

Gln Asp Pro Asn Pro Tyr Ser Phe Gln Ser Asp Val Tyr Ala Tyr Gly
                485                 490                 495

Val Val Leu Tyr Glu Leu Met Thr Gly Ser Leu Pro Tyr Ser His Ile
            500                 505                 510

Gly Cys Arg Asp Gln Ile Ile Phe Met Val Gly Arg Gly Tyr Leu Ser
        515                 520                 525

Pro Asp Leu Ser Lys Ile Ser Ser Asn Cys Pro Lys Ala Met Arg Arg
    530                 535                 540

Leu Leu Ser Asp Cys Leu Lys Phe Gln Arg Glu Glu Arg Pro Leu Phe
545                 550                 555                 560

Pro Gln Ile Leu Ala Thr Ile Glu Leu Leu Gln Arg Ser Leu Pro Lys
                565                 570                 575

Ile Glu Arg Ser Ala Ser Glu Pro Ser Leu His Arg Thr Gln Ala Asp
            580                 585                 590

Glu Leu Pro Ala Cys Leu Leu Ser Ala Ala Arg Leu Val Pro Ile Asp
        595                 600                 605

<210> SEQ ID NO 5
<211> LENGTH: 768
<212> TYPE: PRT
<213> ORGANISM: Homo sapiens

<400> SEQUENCE: 5

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
        50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190
```

```
Glu Cys Cys Ala Val Tyr Arg Ile Gln Asp Gly Glu Lys Lys Pro Ile
            195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
            275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
            355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
                420                 425                 430

Glu Asp Arg Asn Arg Met Lys Thr Leu Gly Arg Arg Asp Ser Ser Asp
            435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
            515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
                580                 585                 590

Gly Asp Phe Gly Leu Ala Thr Glu Lys Ser Arg Trp Ser Gly Ser His
            595                 600                 605
```

```
Gln Phe Glu Gln Leu Ser Gly Ser Ile Leu Trp Met Ala Pro Glu Val
610                 615                 620
Ile Arg Met Gln Asp Lys Asn Pro Tyr Ser Phe Gln Ser Asp Val Tyr
625                 630                 635                 640
Ala Phe Gly Ile Val Leu Tyr Glu Leu Met Thr Gly Gln Leu Pro Tyr
                645                 650                 655
Ser Asn Ile Asn Asn Arg Asp Gln Ile Ile Phe Met Val Gly Arg Gly
                660                 665                 670
Tyr Leu Ser Pro Asp Leu Ser Lys Val Arg Ser Asn Cys Pro Lys Ala
            675                 680                 685
Met Lys Arg Leu Met Ala Glu Cys Leu Lys Lys Lys Arg Asp Glu Arg
690                 695                 700
Pro Leu Phe Pro Gln Ile Leu Ala Ser Ile Glu Leu Leu Ala Arg Ser
705                 710                 715                 720
Leu Pro Lys Ile His Arg Ser Ala Ser Glu Pro Ser Leu Asn Arg Ala
                725                 730                 735
Gly Phe Gln Thr Glu Asp Phe Ser Leu Tyr Ala Cys Ala Ser Pro Lys
                740                 745                 750
Thr Pro Ile Gln Ala Gly Gly Tyr Gly Ala Phe Pro Val His Ile Asp
            755                 760                 765

<210> SEQ ID NO 6
<211> LENGTH: 768
<212> TYPE: PRT
<213> ORGANISM: Homo sapiens

<400> SEQUENCE: 6

Met Ala Ala Leu Ser Gly Gly Gly Gly Gly Gly Ala Glu Pro Gly Gln
1               5                   10                  15
Ala Leu Phe Asn Gly Asp Met Glu Pro Glu Ala Gly Ala Gly Ala Gly
                20                  25                  30
Ala Ala Ala Ser Ser Ala Ala Asp Pro Ala Ile Pro Glu Glu Val Trp
            35                  40                  45
Asn Ile Lys Gln Met Ile Lys Leu Thr Gln Glu His Ile Glu Ala Leu
50                  55                  60
Leu Asp Lys Phe Gly Gly Glu His Asn Pro Pro Ser Ile Tyr Leu Glu
65                  70                  75                  80
Ala Tyr Glu Glu Tyr Thr Ser Lys Leu Asp Ala Leu Gln Gln Arg Glu
                85                  90                  95
Gln Gln Leu Leu Glu Ser Leu Gly Asn Gly Thr Asp Phe Ser Val Ser
            100                 105                 110
Ser Ser Ala Ser Met Asp Thr Val Thr Ser Ser Ser Ser Ser Ser Leu
            115                 120                 125
Ser Val Leu Pro Ser Ser Leu Ser Val Phe Gln Asn Pro Thr Asp Val
            130                 135                 140
Ala Arg Ser Asn Pro Lys Ser Pro Gln Lys Pro Ile Val Arg Val Phe
145                 150                 155                 160
Leu Pro Asn Lys Gln Arg Thr Val Val Pro Ala Arg Cys Gly Val Thr
                165                 170                 175
Val Arg Asp Ser Leu Lys Lys Ala Leu Met Met Arg Gly Leu Ile Pro
            180                 185                 190
Glu Cys Cys Ala Val Tyr Arg Ile Gln Asp Gly Glu Lys Lys Pro Ile
            195                 200                 205
Gly Trp Asp Thr Asp Ile Ser Trp Leu Thr Gly Glu Glu Leu His Val
210                 215                 220
```

-continued

```
Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
            245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
            325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Ser Thr Thr Gly Leu Ser Ala
385                 390                 395                 400

Thr Pro Pro Ala Ser Leu Pro Gly Ser Leu Thr Asn Val Lys Ala Leu
            405                 410                 415

Gln Lys Ser Pro Gly Pro Gln Arg Glu Arg Lys Ser Ser Ser Ser Ser
                420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
            450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
            485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
            565                 570                 575

Leu Lys Ser Asn Asn Ile Phe Leu His Glu Asp Leu Thr Val Lys Ile
                580                 585                 590

Gly Asp Phe Gly Leu Ala Thr Lys Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640
```

-continued

```
Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His Ile Asp
        755                 760                 765

<210> SEQ ID NO 7
<211> LENGTH: 768
<212> TYPE: PRT
<213> ORGANISM: Homo sapiens

<400> SEQUENCE: 7

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
        50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255
```

```
Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
            325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
            405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
            485                 490                 495

Ala Phe Lys Asn Glu Val Gly Val Leu Arg Lys Thr Arg His Val Asn
        500                 505                 510

Ile Leu Leu Phe Met Gly Tyr Ser Thr Lys Pro Gln Leu Ala Ile Val
    515                 520                 525

Thr Gln Trp Cys Glu Gly Ser Ser Leu Tyr His His Leu His Ile Ile
530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
            565                 570                 575

Leu Lys Ser Asn Asn Ile Phe Leu His Glu Asp Leu Thr Val Lys Ile
        580                 585                 590

Gly Asp Phe Gly Leu Ala Thr Arg Lys Ser Arg Trp Ser Gly Ser His
    595                 600                 605

Gln Phe Glu Gln Leu Ser Gly Ser Ile Leu Trp Met Ala Pro Glu Val
            610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
            645                 650                 655

Ser Asn Ile Asn Asn Arg Asp Gln Ile Ile Phe Met Val Gly Arg Gly
        660                 665                 670
```

```
Tyr Leu Ser Pro Asp Leu Ser Lys Val Arg Ser Asn Cys Pro Lys Ala
            675                 680                 685

Met Lys Arg Leu Met Ala Glu Cys Leu Lys Lys Arg Asp Glu Arg
690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
                740                 745                 750

Thr Pro Ile Gln Ala Gly Gly Tyr Gly Ala Phe Pro Val His Ile Asp
            755                 760                 765

<210> SEQ ID NO 8
<211> LENGTH: 768
<212> TYPE: PRT
<213> ORGANISM: Homo sapiens

<400> SEQUENCE: 8

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285
```

```
Leu Phe Val Ser Lys Phe Phe Glu His His Pro Ile Pro Gln Glu Glu
            290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
            355                 360                 365

Val His Ile Asn Thr Ile Glu Pro Val Asn Ile Asp Asp Leu Ile Arg
370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
                420                 425                 430

Glu Asp Arg Asn Arg Met Lys Thr Leu Gly Arg Arg Asp Ser Ser Asp
            435                 440                 445

Asp Trp Glu Ile Pro Asp Gly Gln Ile Thr Val Gly Gln Arg Ile Gly
450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
            515                 520                 525

Thr Gln Trp Cys Glu Gly Ser Ser Leu Tyr His His Leu His Ile Ile
530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Gly Phe Gly Leu Ala Thr Val Lys Ser Arg Trp Ser Gly Ser His
            595                 600                 605

Gln Phe Glu Gln Leu Ser Gly Ser Ile Leu Trp Met Ala Pro Glu Val
610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
                660                 665                 670

Tyr Leu Ser Pro Asp Leu Ser Lys Val Arg Ser Asn Cys Pro Lys Ala
            675                 680                 685

Met Lys Arg Leu Met Ala Glu Cys Leu Lys Lys Arg Asp Glu Arg
            690                 695                 700
```

```
Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
            725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His Ile Asp
            755                 760                 765

<210> SEQ ID NO 9
<211> LENGTH: 768
<212> TYPE: PRT
<213> ORGANISM: Homo sapiens

<400> SEQUENCE: 9

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
290                 295                 300

Ala Ser Leu Ala Glu Thr Ala Leu Thr Ser Gly Ser Ser Pro Ser Ala
305                 310                 315                 320
```

```
Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
                355                 360                 365

Val His Ile Asn Thr Ile Glu Pro Val Asn Ile Asp Asp Leu Ile Arg
                370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
                420                 425                 430

Glu Asp Arg Asn Arg Met Lys Thr Leu Gly Arg Arg Asp Ser Ser Asp
                435                 440                 445

Asp Trp Glu Ile Pro Asp Gly Gln Ile Thr Val Gly Gln Arg Ile Gly
                450                 455                 460

Ser Gly Ser Phe Ala Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
                515                 520                 525

Thr Gln Trp Cys Glu Gly Ser Ser Leu Tyr His His Leu His Ile Ile
                530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
                580                 585                 590

Gly Asp Phe Gly Leu Ala Thr Val Lys Ser Arg Trp Ser Gly Ser His
595                 600                 605

Gln Phe Glu Gln Leu Ser Gly Ser Ile Leu Trp Met Ala Pro Glu Val
                610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
                660                 665                 670

Tyr Leu Ser Pro Asp Leu Ser Lys Val Arg Ser Asn Cys Pro Lys Ala
                675                 680                 685

Met Lys Arg Leu Met Ala Glu Cys Leu Lys Lys Arg Asp Glu Arg
                690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735
```

Gly Phe Gln Thr Glu Asp Phe Ser Leu Tyr Ala Cys Ala Ser Pro Lys
                740                 745                 750

Thr Pro Ile Gln Ala Gly Gly Tyr Gly Ala Phe Pro Val His Ile Asp
        755                 760                 765

<210> SEQ ID NO 10
<211> LENGTH: 768
<212> TYPE: PRT
<213> ORGANISM: Homo sapiens

<400> SEQUENCE: 10

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

```
His Arg Asn Gln Phe Gly Gln Arg Asp Arg Ser Ser Ala Pro Asn
            355                 360                 365
Val His Ile Asn Thr Ile Glu Pro Val Asn Ile Asp Asp Leu Ile Arg
    370                 375                 380
Asp Gln Gly Phe Arg Gly Asp Gly Gly Ser Thr Thr Gly Leu Ser Ala
385                 390                 395                 400
Thr Pro Pro Ala Ser Leu Pro Gly Ser Leu Thr Asn Val Lys Ala Leu
                405                 410                 415
Gln Lys Ser Pro Gly Pro Gln Arg Glu Arg Lys Ser Ser Ser Ser Ser
                420                 425                 430
Glu Asp Arg Asn Arg Met Lys Thr Leu Gly Arg Arg Asp Ser Ser Asp
        435                 440                 445
Asp Trp Glu Ile Pro Asp Gly Gln Ile Thr Val Gly Gln Arg Ile Gly
    450                 455                 460
Ser Gly Ser Phe Gly Thr Val Tyr Lys Gly Lys Trp His Gly Asp Val
465                 470                 475                 480
Ala Val Lys Met Leu Asn Val Thr Ala Pro Thr Pro Gln Gln Leu Gln
                485                 490                 495
Ala Phe Lys Asn Glu Val Gly Val Leu Arg Lys Thr Arg His Val Asn
                500                 505                 510
Ile Leu Leu Phe Met Gly Tyr Ser Thr Lys Pro Gln Leu Ala Ile Val
            515                 520                 525
Thr Gln Trp Cys Glu Gly Ser Ser Leu Tyr His His Leu His Ile Ile
        530                 535                 540
Glu Thr Lys Phe Glu Met Ile Lys Leu Ile Asp Ile Ala Arg Gln Thr
545                 550                 555                 560
Ala Gln Gly Met Asp Tyr Leu His Ala Lys Ser Ile Ile His Arg Asp
                565                 570                 575
Leu Lys Ser Asn Asn Ile Phe Leu His Glu Asp Leu Thr Val Lys Ile
                580                 585                 590
Gly Asp Phe Gly Leu Ala Thr Val Glu Ser Arg Trp Ser Gly Ser His
            595                 600                 605
Gln Phe Glu Gln Leu Ser Gly Ser Ile Leu Trp Met Ala Pro Glu Val
        610                 615                 620
Ile Arg Met Gln Asp Lys Asn Pro Tyr Ser Phe Gln Ser Asp Val Tyr
625                 630                 635                 640
Ala Phe Gly Ile Val Leu Tyr Glu Leu Met Thr Gly Gln Leu Pro Tyr
                645                 650                 655
Ser Asn Ile Asn Asn Arg Asp Gln Ile Ile Phe Met Val Gly Arg Gly
                660                 665                 670
Tyr Leu Ser Pro Asp Leu Ser Lys Val Arg Ser Asn Cys Pro Lys Ala
            675                 680                 685
Met Lys Arg Leu Met Ala Glu Cys Leu Lys Lys Lys Arg Asp Glu Arg
        690                 695                 700
Pro Leu Phe Pro Gln Ile Leu Ala Ser Ile Glu Leu Leu Ala Arg Ser
705                 710                 715                 720
Leu Pro Lys Ile His Arg Ser Ala Ser Glu Pro Ser Leu Asn Arg Ala
                725                 730                 735
Gly Phe Gln Thr Glu Asp Phe Ser Leu Tyr Ala Cys Ala Ser Pro Lys
                740                 745                 750
Thr Pro Ile Gln Ala Gly Gly Tyr Gly Ala Phe Pro Val His Ile Asp
            755                 760                 765
```

```
<210> SEQ ID NO 11
<211> LENGTH: 650
<212> TYPE: PRT
<213> ORGANISM: Homo sapiens

<400> SEQUENCE: 11

Met Glu His Ile Gln Gly Ala Trp Lys Thr Ile Ser Asn Gly Phe Gly
 1               5                  10                  15

Phe Lys Asp Ala Val Phe Asp Gly Ser Ser Cys Ile Ser Pro Thr Ile
                20                  25                  30

Val Gln Gln Phe Gly Tyr Gln Arg Arg Ala Ser Asp Asp Gly Lys Leu
            35                  40                  45

Thr Asp Pro Ser Lys Thr Ser Asn Thr Ile Arg Val Phe Leu Pro Asn
 50                  55                  60

Lys Gln Arg Thr Val Val Asn Val Arg Asn Gly Met Ser Leu His Asp
 65                  70                  75                  80

Cys Leu Met Lys Ala Leu Lys Val Arg Gly Leu Gln Pro Glu Cys Cys
                 85                  90                  95

Ala Val Phe Arg Leu Leu His Glu His Lys Gly Lys Lys Ala Arg Leu
            100                 105                 110

Asp Trp Asn Thr Asp Ala Ala Ser Leu Ile Gly Glu Glu Leu Gln Val
        115                 120                 125

Asp Phe Leu Asp His Val Pro Leu Thr Thr His Asn Phe Ala Arg Lys
130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Leu Thr Ser Thr Pro Asn Val His Met Val Ser Thr Thr Leu Pro Val
            260                 265                 270

Asp Ser Arg Met Ile Glu Asp Ala Ile Arg Ser His Ser Glu Ser Ala
        275                 280                 285

Ser Pro Ser Ala Leu Ser Ser Ser Pro Asn Asn Leu Ser Pro Thr Gly
290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
            340                 345                 350

Thr Arg Ile Gly Ser Gly Ser Phe Gly Thr Val Tyr Lys Gly Lys Trp
        355                 360                 365

His Gly Asp Val Ala Val Lys Ile Leu Lys Val Val Asp Pro Thr Pro
370                 375                 380
```

```
Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
            405                 410                 415

Leu Ala Ile Val Thr Gln Trp Cys Glu Gly Ser Ser Leu Tyr Lys His
        420                 425                 430

Leu His Val Gln Glu Thr Lys Phe Gln Met Phe Gln Leu Ile Asp Ile
    435                 440                 445

Ala Arg Gln Thr Ala Gln Gly Met Asp Tyr Leu His Ala Lys Asn Ile
450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
            485                 490                 495

Ser Gly Ser Gln Gln Val Glu Gln Pro Thr Gly Ser Val Leu Trp Met
        500                 505                 510

Ala Pro Glu Val Ile Arg Met Gln Asp Asn Asn Pro Phe Ser Phe Gln
    515                 520                 525

Ser Asp Val Tyr Ser Tyr Gly Ile Val Leu Tyr Glu Leu Met Thr Gly
530                 535                 540

Glu Leu Pro Tyr Ser His Ile Asn Asn Arg Asp Gln Ile Ile Phe Met
545                 550                 555                 560

Val Gly Arg Gly Tyr Ala Ser Pro Asp Leu Ser Lys Leu Tyr Lys Asn
            565                 570                 575

Cys Pro Lys Ala Met Lys Arg Leu Val Ala Asp Cys Val Lys Lys Val
        580                 585                 590

Lys Glu Glu Arg Pro Leu Phe Pro Gln Ile Leu Ser Ser Ile Glu Leu
    595                 600                 605

Leu Gln His Ser Leu Pro Lys Ile Asn Arg Ser Ala Ser Glu Pro Ser
610                 615                 620

Leu His Arg Ala Ala His Thr Glu Asp Ile Asn Ala Cys Thr Leu Thr
625                 630                 635                 640

Thr Ser Pro Arg Leu Pro Val Phe Ile Asp
            645                 650

<210> SEQ ID NO 12
<211> LENGTH: 650
<212> TYPE: PRT
<213> ORGANISM: Homo sapiens

<400> SEQUENCE: 12

Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
            20                  25                  30

Val Gln Gln Phe Gly Tyr Gln Arg Arg Ala Ser Asp Asp Gly Lys Leu
        35                  40                  45

Thr Asp Pro Ser Lys Thr Ser Asn Thr Ile Arg Val Phe Leu Pro Asn
    50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
```

-continued

```
                100                 105                 110
Asp Trp Asn Thr Asp Ala Ala Ser Leu Ile Gly Glu Glu Leu Gln Val
            115                 120                 125

Asp Phe Leu Asp His Val Pro Leu Thr Thr His Asn Phe Ala Arg Lys
        130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ala Thr Pro Asn Val His Met Val Ser Thr Thr Leu Pro Val
            260                 265                 270

Asp Ser Arg Met Ile Glu Asp Ala Ile Arg Ser His Ser Glu Ser Ala
        275                 280                 285

Ser Pro Ser Ala Leu Ser Ser Pro Asn Asn Leu Ser Pro Thr Gly
        290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
            340                 345                 350

Thr Arg Ile Gly Ser Gly Ser Phe Gly Thr Val Tyr Lys Gly Lys Trp
        355                 360                 365

His Gly Asp Val Ala Val Lys Ile Leu Lys Val Val Asp Pro Thr Pro
        370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
            420                 425                 430

Leu His Val Gln Glu Thr Lys Phe Gln Met Phe Gln Leu Ile Asp Ile
        435                 440                 445

Ala Arg Gln Thr Ala Gln Gly Met Asp Tyr Leu His Ala Lys Asn Ile
        450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
            500                 505                 510

Ala Pro Glu Val Ile Arg Met Gln Asp Asn Asn Pro Phe Ser Phe Gln
        515                 520                 525
```

```
Ser Asp Val Tyr Ser Tyr Gly Ile Val Leu Tyr Glu Leu Met Thr Gly
        530                 535                 540
Glu Leu Pro Tyr Ser His Ile Asn Asn Arg Asp Gln Ile Ile Phe Met
545                 550                 555                 560
Val Gly Arg Gly Tyr Ala Ser Pro Asp Leu Ser Lys Leu Tyr Lys Asn
                565                 570                 575
Cys Pro Lys Ala Met Lys Arg Leu Val Ala Asp Cys Val Lys Lys Val
            580                 585                 590
Lys Glu Glu Arg Pro Leu Phe Pro Gln Ile Leu Ser Ser Ile Glu Leu
        595                 600                 605
Leu Gln His Ser Leu Pro Lys Ile Asn Arg Ser Ala Ser Glu Pro Ser
    610                 615                 620
Leu His Arg Ala Ala His Thr Glu Asp Ile Asn Ala Cys Thr Leu Thr
625                 630                 635                 640
Thr Ser Pro Arg Leu Pro Val Phe Ile Asp
                645                 650

<210> SEQ ID NO 13
<211> LENGTH: 393
<212> TYPE: PRT
<213> ORGANISM: Homo sapiens

<400> SEQUENCE: 13

Met Pro Lys Lys Lys Pro Thr Pro Ile Gln Leu Asn Pro Ala Pro Asp
1               5                   10                  15
Gly Ser Ala Val Asn Gly Thr Ser Ser Ala Glu Thr Asn Leu Glu Ala
            20                  25                  30
Leu Gln Lys Lys Leu Glu Glu Leu Glu Leu Asp Glu Gln Gln Arg Lys
        35                  40                  45
Arg Leu Glu Ala Phe Leu Thr Gln Lys Gln Lys Val Gly Glu Leu Lys
    50                  55                  60
Asp Asp Asp Phe Glu Lys Ile Ser Glu Leu Gly Ala Gly Asn Gly Gly
65                  70                  75                  80
Val Val Phe Lys Val Ser His Lys Pro Ser Gly Leu Val Met Ala Arg
                85                  90                  95
Lys Leu Ile His Leu Glu Ile Lys Pro Ala Ile Arg Asn Gln Ile Ile
            100                 105                 110
Arg Glu Leu Gln Val Leu His Glu Cys Asn Ser Pro Tyr Ile Val Gly
        115                 120                 125
Phe Tyr Gly Ala Phe Tyr Ser Asp Gly Glu Ile Ser Ile Cys Met Glu
    130                 135                 140
His Met Asp Gly Gly Ser Leu Asp Gln Val Leu Lys Lys Ala Gly Arg
145                 150                 155                 160
Ile Pro Glu Gln Ile Leu Gly Lys Val Ser Ile Ala Val Ile Lys Gly
                165                 170                 175
Leu Thr Tyr Leu Arg Glu Lys His Lys Ile Met His Arg Asp Val Lys
            180                 185                 190
Pro Ser Asn Ile Leu Val Asn Ser Arg Gly Glu Ile Lys Leu Cys Asp
        195                 200                 205
Phe Gly Val Ser Gly Gln Leu Ile Asp Ser Met Ala Asn Ser Phe Val
    210                 215                 220
Gly Thr Arg Ser Tyr Met Ser Pro Glu Arg Leu Gln Gly Thr His Tyr
225                 230                 235                 240
Ser Val Gln Ser Asp Ile Trp Ser Met Gly Leu Ser Leu Val Glu Met
```

```
                245                 250                 255
Ala Val Gly Arg Tyr Pro Ile Pro Pro Asp Ala Lys Glu Leu Glu
        260                 265                 270

Leu Met Phe Gly Cys Gln Val Glu Gly Asp Ala Ala Glu Thr Pro Pro
            275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
                340                 345                 350

Lys Gln Leu Met Val His Ala Phe Ile Lys Arg Ser Asp Ala Glu Glu
            355                 360                 365

Val Asp Phe Ala Gly Trp Leu Cys Ser Thr Ile Gly Leu Asn Gln Pro
        370                 375                 380

Ser Thr Pro Thr His Ala Ala Gly Val
385                 390

<210> SEQ ID NO 14
<211> LENGTH: 400
<212> TYPE: PRT
<213> ORGANISM: Homo sapiens

<400> SEQUENCE: 14

Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
            20                  25                  30

Asn Leu Val Asp Leu Gln Lys Lys Leu Glu Glu Leu Glu Leu Asp Glu
        35                  40                  45

Gln Gln Lys Lys Arg Leu Glu Ala Phe Leu Thr Gln Lys Ala Lys Val
    50                  55                  60

Gly Glu Leu Lys Asp Asp Asp Phe Glu Arg Ile Ser Glu Leu Gly Ala
65                  70                  75                  80

Gly Asn Gly Gly Val Val Thr Lys Val Gln His Arg Pro Ser Gly Leu
                85                  90                  95

Ile Met Ala Arg Lys Leu Ile His Leu Glu Ile Lys Pro Ala Ile Arg
            100                 105                 110

Asn Gln Ile Ile Arg Glu Leu Gln Val Leu His Glu Cys Asn Ser Pro
        115                 120                 125

Tyr Ile Val Gly Phe Tyr Gly Ala Phe Tyr Ser Asp Gly Glu Ile Ser
    130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
            180                 185                 190

Arg Asp Val Lys Pro Ser Asn Ile Leu Val Asn Ser Arg Gly Glu Ile
        195                 200                 205

Lys Leu Cys Asp Phe Gly Val Ser Gly Gln Leu Ile Asp Ser Met Ala
    210                 215                 220
```

```
Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
            245                 250                 255

Leu Val Glu Leu Ala Val Gly Arg Tyr Pro Ile Pro Pro Asp Ala
        260                 265                 270

Lys Glu Leu Glu Ala Ile Phe Gly Arg Pro Val Val Asp Gly Glu Glu
        275                 280                 285

Gly Glu Pro His Ser Ile Ser Pro Arg Pro Arg Pro Gly Arg Pro
        290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Pro Lys Leu Pro Asn Gly
                325                 330                 335

Val Phe Thr Pro Asp Phe Gln Glu Phe Val Asn Lys Cys Leu Ile Lys
                340                 345                 350

Asn Pro Ala Glu Arg Ala Asp Leu Lys Met Leu Thr Asn His Thr Phe
            355                 360                 365

Ile Lys Arg Ser Glu Val Glu Glu Val Asp Phe Ala Gly Trp Leu Cys
370                 375                 380

Lys Thr Leu Arg Leu Asn Gln Pro Gly Thr Pro Thr Arg Thr Ala Val
385                 390                 395                 400

<210> SEQ ID NO 15
<211> LENGTH: 393
<212> TYPE: PRT
<213> ORGANISM: Homo sapiens

<400> SEQUENCE: 15

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205
```

Phe Gly Val Ser Gly Gln Leu Ile Asp Ala Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
    370                 375                 380

Ser Thr Pro Thr His Ala Ala Gly Val
385                 390

<210> SEQ ID NO 16
<211> LENGTH: 393
<212> TYPE: PRT
<213> ORGANISM: Homo sapiens

<400> SEQUENCE: 16

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys

```
              180                 185                 190
Pro Ser Asn Ile Leu Val Asn Ser Arg Gly Glu Ile Lys Leu Cys Asp
            195                 200                 205

Phe Gly Val Ser Gly Gln Leu Ile Asp Glu Met Ala Asn Glu Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
        260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
    370                 375                 380

Ser Thr Pro Thr His Ala Ala Gly Val
385                 390

<210> SEQ ID NO 17
<211> LENGTH: 109
<212> TYPE: PRT
<213> ORGANISM: Artificial sequence
<220> FEATURE:
<223> OTHER INFORMATION: Luciferase fragement derived from Renilla
      luciferase protein sequence

<400> SEQUENCE: 17

Ala Ser Lys Val Tyr Asp Pro Glu Gln Arg Lys Arg Met Ile Thr Gly
1               5                   10                  15

Pro Gln Trp Trp Ala Arg Cys Lys Gln Met Asn Val Leu Asp Ser Phe
            20                  25                  30

Ile Asn Tyr Tyr Asp Ser Glu Lys His Ala Glu Asn Ala Val Ile Phe
        35                  40                  45

Leu His Gly Asn Ala Ala Ser Ser Tyr Leu Trp Arg His Val Val Pro
    50                  55                  60

His Ile Glu Pro Val Ala Arg Cys Ile Ile Pro Asp Leu Ile Gly Met
65                  70                  75                  80

Gly Lys Ser Gly Lys Ser Gly Asn Gly Ser Tyr Arg Leu Leu Asp His
                85                  90                  95

Tyr Lys Tyr Leu Thr Ala Trp Phe Glu Leu Leu Asn Leu
            100                 105

<210> SEQ ID NO 18
<211> LENGTH: 201
<212> TYPE: PRT
<213> ORGANISM: Artificial sequence
<220> FEATURE:
```

<223> OTHER INFORMATION: Luciferase fragement derived from Renilla
      luciferase protein sequence

<400> SEQUENCE: 18

Pro Lys Lys Ile Ile Phe Val Gly His Asp Trp Gly Ala Cys Leu Ala
1               5                   10                  15

Phe His Tyr Ser Tyr Glu His Gln Asp Lys Ile Lys Ala Ile Val His
            20                  25                  30

Ala Glu Ser Val Val Asp Val Ile Glu Ser Trp Asp Glu Trp Pro Asp
        35                  40                  45

Ile Glu Glu Asp Ile Ala Leu Ile Lys Ser Glu Glu Gly Glu Lys Met
50                  55                  60

Val Leu Glu Asn Asn Phe Phe Val Glu Thr Met Leu Pro Ser Lys Ile
65                  70                  75                  80

Met Arg Lys Leu Glu Pro Glu Glu Phe Ala Ala Tyr Leu Glu Pro Phe
                85                  90                  95

Lys Glu Lys Gly Glu Val Arg Arg Pro Thr Leu Ser Trp Pro Arg Glu
            100                 105                 110

Ile Pro Leu Val Lys Gly Gly Lys Pro Asp Val Val Gln Ile Val Arg
        115                 120                 125

Asn Tyr Asn Ala Tyr Leu Arg Ala Ser Asp Asp Leu Pro Lys Met Phe
130                 135                 140

Ile Glu Ser Asp Pro Gly Phe Phe Ser Asn Ala Ile Val Glu Gly Ala
145                 150                 155                 160

Lys Lys Phe Pro Asn Thr Glu Phe Val Lys Val Lys Gly Leu His Phe
                165                 170                 175

Ser Gln Glu Asp Ala Pro Asp Glu Met Gly Lys Tyr Ile Lys Ser Phe
            180                 185                 190

Val Glu Arg Val Leu Lys Asn Glu Gln
        195                 200

<210> SEQ ID NO 19
<211> LENGTH: 93
<212> TYPE: PRT
<213> ORGANISM: Artificial sequence
<220> FEATURE:
<223> OTHER INFORMATION: Luciferase fragement derived from Gaussia
      luciferase protein sequence

<400> SEQUENCE: 19

Met Lys Pro Thr Glu Asn Asn Glu Asp Phe Asn Ile Val Ala Val Ala
1               5                   10                  15

Ser Asn Phe Ala Thr Thr Asp Leu Asp Ala Asp Arg Gly Lys Leu Pro
            20                  25                  30

Gly Lys Lys Leu Pro Leu Glu Val Leu Lys Glu Met Glu Ala Asn Ala
        35                  40                  45

Arg Lys Ala Gly Cys Thr Arg Gly Cys Leu Ile Cys Leu Ser His Ile
50                  55                  60

Lys Cys Thr Pro Lys Met Lys Lys Phe Ile Pro Gly Arg Cys His Thr
65                  70                  75                  80

Tyr Glu Gly Asp Lys Glu Ser Ala Gln Gly Gly Ile Gly
                85                  90

<210> SEQ ID NO 20
<211> LENGTH: 76
<212> TYPE: PRT
<213> ORGANISM: Artificial Sequence
<220> FEATURE:

<223> OTHER INFORMATION: Luciferase fragement derived from Gaussia
luciferase protein sequence

<400> SEQUENCE: 20

Glu Ala Ile Val Asp Ile Pro Glu Ile Pro Gly Phe Lys Asp Leu Glu
1               5                   10                  15

Pro Met Glu Gln Phe Ile Ala Gln Val Asp Leu Cys Val Asp Cys Thr
            20                  25                  30

Thr Gly Cys Leu Lys Gly Leu Ala Asn Val Gln Cys Ser Asp Leu Leu
        35                  40                  45

Lys Lys Trp Leu Pro Gln Arg Cys Ala Thr Phe Ala Ser Lys Ile Gln
    50                  55                  60

Gly Gln Val Asp Lys Ile Lys Gly Ala Gly Gly Asp
65                  70                  75

<210> SEQ ID NO 21
<211> LENGTH: 10
<212> TYPE: PRT
<213> ORGANISM: Artificial Sequence
<220> FEATURE:
<223> OTHER INFORMATION: Potential linker for fused protein construct

<400> SEQUENCE: 21

Gly Gly Gly Gly Ser Gly Gly Gly Gly Ser
1               5                   10

<210> SEQ ID NO 22
<211> LENGTH: 1104
<212> TYPE: PRT
<213> ORGANISM: Artificial sequence
<220> FEATURE:
<223> OTHER INFORMATION: BRAF(wt) reporter comprising an N-terminal
Renilla luciferase fragment, a linker, a BRAF(wt) sequence, a
linker, and a C-terminal Renilla luciferase fragment

<400> SEQUENCE: 22

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
            85                  90                  95

His Tyr Lys Tyr Leu Thr Ala Trp Phe Glu Leu Leu Asn Leu Ile Asp
            100                 105                 110

Gly Gly Gly Gly Ser Gly Gly Gly Gly Ser Ser Gly Ala Ala Leu Ser
        115                 120                 125

Gly Gly Gly Gly Gly Ala Glu Pro Gly Gln Ala Leu Phe Asn Gly
    130                 135                 140

Asp Met Glu Pro Glu Ala Gly Ala Gly Ala Ala Ala Ser Ser
145                 150                 155                 160

Ala Ala Asp Pro Ala Ile Pro Glu Glu Val Trp Asn Ile Lys Gln Met
            165                 170                 175

Ile Lys Leu Thr Gln Glu His Ile Glu Ala Leu Leu Asp Lys Phe Gly

```
            180                 185                 190
Gly Glu His Asn Pro Pro Ser Ile Tyr Leu Glu Ala Tyr Glu Glu Tyr
            195                 200                 205
Thr Ser Lys Leu Asp Ala Leu Gln Gln Arg Glu Gln Gln Leu Leu Glu
            210                 215                 220
Ser Leu Gly Asn Gly Thr Asp Phe Ser Val Ser Ser Ala Ser Met
225                 230                 235                 240
Asp Thr Val Thr Ser Ser Ser Ser Ser Leu Ser Val Leu Pro Ser
                245                 250                 255
Ser Leu Ser Val Phe Gln Asn Pro Thr Asp Val Ala Arg Ser Asn Pro
            260                 265                 270
Lys Ser Pro Gln Lys Pro Ile Val Arg Val Phe Leu Pro Asn Lys Gln
            275                 280                 285
Arg Thr Val Val Pro Ala Arg Cys Gly Val Thr Val Arg Asp Ser Leu
            290                 295                 300
Lys Lys Ala Leu Met Met Arg Gly Leu Ile Pro Glu Cys Cys Ala Val
305                 310                 315                 320
Tyr Arg Ile Gln Asp Gly Glu Lys Lys Pro Ile Gly Trp Asp Thr Asp
                325                 330                 335
Ile Ser Trp Leu Thr Gly Glu Glu Leu His Val Glu Val Leu Glu Asn
            340                 345                 350
Val Pro Leu Thr Thr His Asn Phe Val Arg Lys Thr Phe Phe Thr Leu
            355                 360                 365
Ala Phe Cys Asp Phe Cys Arg Lys Leu Leu Phe Gln Gly Phe Arg Cys
            370                 375                 380
Gln Thr Cys Gly Tyr Lys Phe His Gln Arg Cys Ser Thr Glu Val Pro
385                 390                 395                 400
Leu Met Cys Val Asn Tyr Asp Gln Leu Asp Leu Leu Phe Val Ser Lys
                405                 410                 415
Phe Phe Glu His His Pro Ile Pro Gln Glu Glu Ala Ser Leu Ala Glu
                420                 425                 430
Thr Ala Leu Thr Ser Gly Ser Ser Pro Ser Ala Pro Ala Ser Asp Ser
            435                 440                 445
Ile Gly Pro Gln Ile Leu Thr Ser Pro Ser Pro Ser Lys Ser Ile Pro
            450                 455                 460
Ile Pro Gln Pro Phe Arg Pro Ala Asp Glu Asp His Arg Asn Gln Phe
465                 470                 475                 480
Gly Gln Arg Asp Arg Ser Ser Ala Pro Asn Val His Ile Asn Thr
                485                 490                 495
Ile Glu Pro Val Asn Ile Asp Asp Leu Ile Arg Asp Gln Gly Phe Arg
            500                 505                 510
Gly Asp Gly Gly Ser Thr Thr Gly Leu Ser Ala Thr Pro Pro Ala Ser
            515                 520                 525
Leu Pro Gly Ser Leu Thr Asn Val Lys Ala Leu Gln Lys Ser Pro Gly
            530                 535                 540
Pro Gln Arg Glu Arg Lys Ser Ser Ser Ser Glu Asp Arg Asn Arg
545                 550                 555                 560
Met Lys Thr Leu Gly Arg Arg Asp Ser Ser Asp Asp Trp Glu Ile Pro
                565                 570                 575
Asp Gly Gln Ile Thr Val Gly Gln Arg Ile Gly Ser Gly Ser Phe Gly
            580                 585                 590
Thr Val Tyr Lys Gly Lys Trp His Gly Asp Val Ala Val Lys Met Leu
            595                 600                 605
```

```
Asn Val Thr Ala Pro Thr Pro Gln Gln Leu Gln Ala Phe Lys Asn Glu
        610                 615                 620

Val Gly Val Leu Arg Lys Thr Arg His Val Asn Ile Leu Leu Phe Met
625                 630                 635                 640

Gly Tyr Ser Thr Lys Pro Gln Leu Ala Ile Val Thr Gln Trp Cys Glu
                645                 650                 655

Gly Ser Ser Leu Tyr His His Leu His Ile Ile Glu Thr Lys Phe Glu
                660                 665                 670

Met Ile Lys Leu Ile Asp Ile Ala Arg Gln Thr Ala Gln Gly Met Asp
            675                 680                 685

Tyr Leu His Ala Lys Ser Ile Ile His Arg Asp Leu Lys Ser Asn Asn
        690                 695                 700

Ile Phe Leu His Glu Asp Leu Thr Val Lys Ile Gly Asp Phe Gly Leu
705                 710                 715                 720

Ala Thr Val Lys Ser Arg Trp Ser Gly Ser His Gln Phe Glu Gln Leu
                725                 730                 735

Ser Gly Ser Ile Leu Trp Met Ala Pro Glu Val Ile Arg Met Gln Asp
                740                 745                 750

Lys Asn Pro Tyr Ser Phe Gln Ser Asp Val Tyr Ala Phe Gly Ile Val
            755                 760                 765

Leu Tyr Glu Leu Met Thr Gly Gln Leu Pro Tyr Ser Asn Ile Asn Asn
770                 775                 780

Arg Asp Gln Ile Ile Phe Met Val Gly Arg Gly Tyr Leu Ser Pro Asp
785                 790                 795                 800

Leu Ser Lys Val Arg Ser Asn Cys Pro Lys Ala Met Lys Arg Leu Met
                805                 810                 815

Ala Glu Cys Leu Lys Lys Lys Arg Asp Glu Arg Pro Leu Phe Pro Gln
                820                 825                 830

Ile Leu Ala Ser Ile Glu Leu Leu Ala Arg Ser Leu Pro Lys Ile His
            835                 840                 845

Arg Ser Ala Ser Glu Pro Ser Leu Asn Arg Ala Gly Phe Gln Thr Glu
        850                 855                 860

Asp Phe Ser Leu Tyr Ala Cys Ala Ser Pro Lys Thr Pro Ile Gln Ala
865                 870                 875                 880

Gly Gly Tyr Gly Ala Phe Pro Val His Ser Arg Gly Gly Gly Ser
                885                 890                 895

Gly Gly Gly Gly Ser Ser Gly Pro Lys Lys Ile Ile Phe Val Gly His
            900                 905                 910

Asp Trp Gly Ala Cys Leu Ala Phe His Tyr Ser Tyr Glu His Gln Asp
        915                 920                 925

Lys Ile Lys Ala Ile Val His Ala Glu Ser Val Val Asp Val Ile Glu
        930                 935                 940

Ser Trp Asp Glu Trp Pro Asp Ile Glu Glu Asp Ile Ala Leu Ile Lys
945                 950                 955                 960

Ser Glu Glu Gly Glu Lys Met Val Leu Glu Asn Asn Phe Phe Val Glu
                965                 970                 975

Thr Met Leu Pro Ser Lys Ile Met Arg Lys Leu Glu Pro Glu Glu Phe
                980                 985                 990

Ala Ala Tyr Leu Glu Pro Phe Lys Glu Lys Gly Glu Val Arg Arg Pro
            995                1000                1005

Thr Leu Ser Trp Pro Arg Glu Ile Pro Leu Val Lys Gly Gly Lys
        1010                1015                1020
```

```
Pro Asp Val Val Gln Ile Val Arg Asn Tyr Asn Ala Tyr Leu Arg
    1025                1030                1035

Ala Ser Asp Asp Leu Pro Lys Met Phe Ile Glu Ser Asp Pro Gly
    1040                1045                1050

Phe Phe Ser Asn Ala Ile Val Glu Gly Ala Lys Lys Phe Pro Asn
    1055                1060                1065

Thr Glu Phe Val Lys Val Lys Gly Leu His Phe Ser Gln Glu Asp
    1070                1075                1080

Ala Pro Asp Glu Met Gly Lys Tyr Ile Lys Ser Phe Val Glu Arg
    1085                1090                1095

Val Leu Lys Asn Glu Gln
    1100

<210> SEQ ID NO 23
<211> LENGTH: 731
<212> TYPE: PRT
<213> ORGANISM: Artificial sequence
<220> FEATURE:
<223> OTHER INFORMATION: MEK1(wt) reporter comprising an N-terminal
      Renilla luciferase fragment, a linker, a MEK1(wt) sequence, a
      linker, and a C-terminal Renilla luciferase fragment

<400> SEQUENCE: 23

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Ile Asp
            100                 105                 110

Gly Gly Gly Gly Ser Gly Gly Gly Ser Ser Gly Pro Lys Lys Lys
        115                 120                 125

Pro Thr Pro Ile Gln Leu Asn Pro Ala Pro Asp Gly Ser Ala Val Asn
    130                 135                 140

Gly Thr Ser Ser Ala Glu Thr Asn Leu Glu Ala Leu Gln Lys Lys Leu
145                 150                 155                 160

Glu Glu Leu Glu Leu Asp Glu Gln Gln Arg Lys Arg Leu Glu Ala Phe
                165                 170                 175

Leu Thr Gln Lys Gln Lys Val Gly Glu Leu Lys Asp Asp Asp Phe Glu
            180                 185                 190

Lys Ile Ser Glu Leu Gly Ala Gly Asn Gly Gly Val Val Phe Lys Val
        195                 200                 205

Ser His Lys Pro Ser Gly Leu Val Met Ala Arg Lys Leu Ile His Leu
    210                 215                 220

Glu Ile Lys Pro Ala Ile Arg Asn Gln Ile Ile Arg Glu Leu Gln Val
225                 230                 235                 240

Leu His Glu Cys Asn Ser Pro Tyr Ile Val Gly Phe Tyr Gly Ala Phe
                245                 250                 255

Tyr Ser Asp Gly Glu Ile Ser Ile Cys Met Glu His Met Asp Gly Gly
```

```
                 260                 265                 270
Ser Leu Asp Gln Val Leu Lys Lys Ala Gly Arg Ile Pro Glu Gln Ile
            275                 280                 285

Leu Gly Lys Val Ser Ile Ala Val Ile Lys Gly Leu Thr Tyr Leu Arg
        290                 295                 300

Glu Lys His Lys Ile Met His Arg Asp Val Lys Pro Ser Asn Ile Leu
305                 310                 315                 320

Val Asn Ser Arg Gly Glu Ile Lys Leu Cys Asp Phe Gly Val Ser Gly
                325                 330                 335

Gln Leu Ile Asp Ser Met Ala Asn Ser Phe Val Gly Thr Arg Ser Tyr
            340                 345                 350

Met Ser Pro Glu Arg Leu Gln Gly Thr His Tyr Ser Val Gln Ser Asp
        355                 360                 365

Ile Trp Ser Met Gly Leu Ser Leu Val Glu Met Ala Val Gly Arg Tyr
    370                 375                 380

Pro Ile Pro Pro Pro Asp Ala Lys Glu Leu Glu Leu Met Phe Gly Cys
385                 390                 395                 400

Gln Val Glu Gly Asp Ala Ala Glu Thr Pro Pro Arg Pro Arg Thr Pro
                405                 410                 415

Gly Arg Pro Leu Ser Ser Tyr Gly Met Asp Ser Arg Pro Pro Met Ala
            420                 425                 430

Ile Phe Glu Leu Leu Asp Tyr Ile Val Asn Glu Pro Pro Pro Lys Leu
        435                 440                 445

Pro Ser Ala Val Phe Ser Leu Glu Phe Gln Asp Phe Val Asn Lys Cys
    450                 455                 460

Leu Ile Lys Asn Pro Ala Glu Arg Ala Asp Leu Lys Gln Leu Met Val
465                 470                 475                 480

His Ala Phe Ile Lys Arg Ser Asp Ala Glu Glu Val Asp Phe Ala Gly
                485                 490                 495

Trp Leu Cys Ser Thr Ile Gly Leu Asn Gln Pro Ser Thr Pro Thr His
            500                 505                 510

Ala Ala Gly Val Ser Arg Gly Gly Gly Ser Gly Gly Gly Gly Gly Ser
        515                 520                 525

Ser Gly Pro Lys Lys Ile Ile Phe Val Gly His Asp Trp Gly Ala Cys
    530                 535                 540

Leu Ala Phe His Tyr Ser Tyr Glu His Gln Asp Lys Ile Lys Ala Ile
545                 550                 555                 560

Val His Ala Glu Ser Val Val Asp Val Ile Glu Ser Trp Asp Glu Trp
                565                 570                 575

Pro Asp Ile Glu Glu Asp Ile Ala Leu Ile Lys Ser Glu Glu Gly Glu
            580                 585                 590

Lys Met Val Leu Glu Asn Asn Phe Phe Val Glu Thr Met Leu Pro Ser
        595                 600                 605

Lys Ile Met Arg Lys Leu Glu Pro Glu Glu Phe Ala Ala Tyr Leu Glu
    610                 615                 620

Pro Phe Lys Glu Lys Gly Glu Val Arg Arg Pro Thr Leu Ser Trp Pro
625                 630                 635                 640

Arg Glu Ile Pro Leu Val Lys Gly Gly Lys Pro Asp Val Val Gln Ile
                645                 650                 655

Val Arg Asn Tyr Asn Ala Tyr Leu Arg Ala Ser Asp Asp Leu Pro Lys
            660                 665                 670

Met Phe Ile Glu Ser Asp Pro Gly Phe Phe Ser Asn Ala Ile Val Glu
        675                 680                 685
```

Gly Ala Lys Lys Phe Pro Asn Thr Glu Phe Val Lys Val Lys Gly Leu
            690                 695                 700                 705

His Phe Ser Gln Glu Asp Ala Pro Asp Glu Met Gly Lys Tyr Ile Lys
705                 710                 715                 720

Ser Phe Val Glu Arg Val Leu Lys Asn Glu Gln
                725                 730

<210> SEQ ID NO 24
<211> LENGTH: 962
<212> TYPE: PRT
<213> ORGANISM: Artificial Sequence
<220> FEATURE:
<223> OTHER INFORMATION: BRAF(wt) reporter comprising an N-terminal
      Gaussia luciferase fragment, a linker, a BRAF(wt) sequence, a
      linker, and a C-terminal Gaussia luciferase fragment

<400> SEQUENCE: 24

Met Lys Pro Thr Glu Asn Asn Glu Asp Phe Asn Ile Val Ala Val Ala
1               5                   10                  15

Ser Asn Phe Ala Thr Thr Asp Leu Asp Ala Asp Arg Gly Lys Leu Pro
                20                  25                  30

Gly Lys Lys Leu Pro Leu Glu Val Leu Lys Glu Met Glu Ala Asn Ala
            35                  40                  45

Arg Lys Ala Gly Cys Thr Arg Gly Cys Leu Ile Cys Leu Ser His Ile
50                  55                  60

Lys Cys Thr Pro Lys Met Lys Lys Phe Ile Pro Gly Arg Cys His Thr
65                  70                  75                  80

Tyr Glu Gly Asp Lys Glu Ser Ala Gln Gly Gly Ile Gly Ile Asp Gly
                85                  90                  95

Gly Gly Gly Ser Gly Gly Gly Ser Gly Ala Ala Leu Ser Gly
            100                 105                 110

Gly Gly Gly Gly Gly Ala Glu Pro Gly Gln Ala Leu Phe Asn Gly Asp
            115                 120                 125

Met Glu Pro Glu Ala Gly Ala Gly Ala Gly Ala Ala Ser Ser Ala
130                 135                 140

Ala Asp Pro Ala Ile Pro Glu Glu Val Trp Asn Ile Lys Gln Met Ile
145                 150                 155                 160

Lys Leu Thr Gln Glu His Ile Glu Ala Leu Leu Asp Lys Phe Gly Gly
                165                 170                 175

Glu His Asn Pro Pro Ser Ile Tyr Leu Glu Ala Tyr Glu Glu Tyr Thr
            180                 185                 190

Ser Lys Leu Asp Ala Leu Gln Gln Arg Glu Gln Gln Leu Leu Glu Ser
        195                 200                 205

Leu Gly Asn Gly Thr Asp Phe Ser Val Ser Ser Ser Ala Ser Met Asp
210                 215                 220

Thr Val Thr Ser Ser Ser Ser Ser Ser Leu Ser Val Leu Pro Ser Ser
225                 230                 235                 240

Leu Ser Val Phe Gln Asn Pro Thr Asp Val Ala Arg Ser Asn Pro Lys
                245                 250                 255

Ser Pro Gln Lys Pro Ile Val Arg Val Phe Leu Pro Asn Lys Gln Arg
            260                 265                 270

Thr Val Val Pro Ala Arg Cys Gly Val Thr Val Arg Asp Ser Leu Lys
        275                 280                 285

Lys Ala Leu Met Met Arg Gly Leu Ile Pro Glu Cys Cys Ala Val Tyr
        290                 295                 300

```
Arg Ile Gln Asp Gly Glu Lys Lys Pro Ile Gly Trp Asp Thr Asp Ile
305                 310                 315                 320

Ser Trp Leu Thr Gly Glu Leu His Val Glu Val Leu Glu Asn Val
            325                 330                 335

Pro Leu Thr Thr His Asn Phe Val Arg Lys Thr Phe Thr Leu Ala
                340                 345                 350

Phe Cys Asp Phe Cys Arg Lys Leu Leu Phe Gln Gly Phe Arg Cys Gln
            355                 360                 365

Thr Cys Gly Tyr Lys Phe His Gln Arg Cys Ser Thr Glu Val Pro Leu
            370                 375                 380

Met Cys Val Asn Tyr Asp Gln Leu Asp Leu Leu Phe Val Ser Lys Phe
385                 390                 395                 400

Phe Glu His His Pro Ile Pro Gln Glu Ala Ser Leu Ala Glu Thr
                405                 410                 415

Ala Leu Thr Ser Gly Ser Ser Pro Ser Ala Pro Ala Ser Asp Ser Ile
            420                 425                 430

Gly Pro Gln Ile Leu Thr Ser Pro Ser Pro Ser Lys Ser Ile Pro Ile
                435                 440                 445

Pro Gln Pro Phe Arg Pro Ala Asp Glu Asp His Arg Asn Gln Phe Gly
    450                 455                 460

Gln Arg Asp Arg Ser Ser Ser Ala Pro Asn Val His Ile Asn Thr Ile
465                 470                 475                 480

Glu Pro Val Asn Ile Asp Asp Leu Ile Arg Asp Gln Gly Phe Arg Gly
                485                 490                 495

Asp Gly Gly Ser Thr Thr Gly Leu Ser Ala Thr Pro Ala Ser Leu
        500                 505                 510

Pro Gly Ser Leu Thr Asn Val Lys Ala Leu Gln Lys Ser Pro Gly Pro
    515                 520                 525

Gln Arg Glu Arg Lys Ser Ser Ser Ser Glu Asp Arg Asn Arg Met
        530                 535                 540

Lys Thr Leu Gly Arg Arg Asp Ser Ser Asp Asp Trp Glu Ile Pro Asp
545                 550                 555                 560

Gly Gln Ile Thr Val Gly Gln Arg Ile Gly Ser Gly Ser Phe Gly Thr
                565                 570                 575

Val Tyr Lys Gly Lys Trp His Gly Asp Val Ala Val Lys Met Leu Asn
            580                 585                 590

Val Thr Ala Pro Thr Pro Gln Gln Leu Gln Ala Phe Lys Asn Glu Val
            595                 600                 605

Gly Val Leu Arg Lys Thr Arg His Val Asn Ile Leu Leu Phe Met Gly
            610                 615                 620

Tyr Ser Thr Lys Pro Gln Leu Ala Ile Val Thr Gln Trp Cys Glu Gly
625                 630                 635                 640

Ser Ser Leu Tyr His His Leu His Ile Glu Thr Lys Phe Glu Met
            645                 650                 655

Ile Lys Leu Ile Asp Ile Ala Arg Gln Thr Ala Gln Gly Met Asp Tyr
            660                 665                 670

Leu His Ala Lys Ser Ile Ile His Arg Asp Leu Lys Ser Asn Asn Ile
    675                 680                 685

Phe Leu His Glu Asp Leu Thr Val Lys Ile Gly Asp Phe Gly Leu Ala
    690                 695                 700

Thr Val Lys Ser Arg Trp Ser Gly Ser His Gln Phe Glu Gln Leu Ser
705                 710                 715                 720

Gly Ser Ile Leu Trp Met Ala Pro Glu Val Ile Arg Met Gln Asp Lys
```

-continued

```
                725                 730                 735
Asn Pro Tyr Ser Phe Gln Ser Asp Val Tyr Ala Phe Gly Ile Val Leu
            740                 745                 750

Tyr Glu Leu Met Thr Gly Gln Leu Pro Tyr Ser Asn Ile Asn Asn Arg
            755                 760                 765

Asp Gln Ile Ile Phe Met Val Gly Arg Gly Tyr Leu Ser Pro Asp Leu
            770                 775                 780

Ser Lys Val Arg Ser Asn Cys Pro Lys Ala Met Lys Arg Leu Met Ala
785                 790                 795                 800

Glu Cys Leu Lys Lys Lys Arg Asp Glu Arg Pro Leu Phe Pro Gln Ile
                805                 810                 815

Leu Ala Ser Ile Glu Leu Leu Ala Arg Ser Leu Pro Lys Ile His Arg
            820                 825                 830

Ser Ala Ser Glu Pro Ser Leu Asn Arg Ala Gly Phe Gln Thr Glu Asp
            835                 840                 845

Phe Ser Leu Tyr Ala Cys Ala Ser Pro Lys Thr Pro Ile Gln Ala Gly
            850                 855                 860

Gly Tyr Gly Ala Phe Pro Val His Ser Arg Gly Gly Gly Ser Gly
865                 870                 875                 880

Gly Gly Gly Ser Ser Gly Glu Ala Ile Val Asp Ile Pro Glu Ile Pro
                885                 890                 895

Gly Phe Lys Asp Leu Glu Pro Met Glu Gln Phe Ile Ala Gln Val Asp
            900                 905                 910

Leu Cys Val Asp Cys Thr Thr Gly Cys Leu Lys Gly Leu Ala Asn Val
            915                 920                 925

Gln Cys Ser Asp Leu Leu Lys Lys Trp Leu Pro Gln Arg Cys Ala Thr
930                 935                 940

Phe Ala Ser Lys Ile Gln Gly Gln Val Asp Lys Ile Lys Gly Ala Gly
945                 950                 955                 960

Gly Asp
```

<210> SEQ ID NO 25
<211> LENGTH: 194
<212> TYPE: PRT
<213> ORGANISM: Homo sapiens

<400> SEQUENCE: 25

```
Met Glu Glu Lys Leu Lys Lys Thr Lys Ile Ile Phe Val Val Gly Gly
1               5                   10                  15

Pro Gly Ser Gly Lys Gly Thr Gln Cys Glu Lys Ile Val Gln Lys Tyr
            20                  25                  30

Gly Tyr Thr His Leu Ser Thr Gly Asp Leu Leu Arg Ser Glu Val Ser
        35                  40                  45

Ser Gly Ser Ala Arg Gly Lys Lys Leu Ser Glu Ile Met Glu Lys Gly
    50                  55                  60

Gln Leu Val Pro Leu Glu Thr Val Leu Asp Met Leu Arg Asp Ala Met
65                  70                  75                  80

Val Ala Lys Val Asn Thr Ser Lys Gly Phe Leu Ile Asp Gly Tyr Pro
                85                  90                  95

Arg Glu Val Gln Gln Gly Glu Glu Phe Glu Arg Arg Ile Gly Gln Pro
            100                 105                 110

Thr Leu Leu Leu Tyr Val Asp Ala Gly Pro Glu Thr Met Thr Gln Arg
        115                 120                 125

Leu Leu Lys Arg Gly Glu Thr Ser Gly Arg Val Asp Asp Asn Glu Glu
```

```
            130                 135                 140
Thr Ile Lys Lys Arg Leu Glu Thr Tyr Tyr Lys Ala Thr Glu Pro Val
145                 150                 155                 160

Ile Ala Phe Tyr Glu Lys Arg Gly Ile Val Arg Lys Val Asn Ala Glu
                165                 170                 175

Gly Ser Val Asp Ser Val Phe Ser Gln Val Cys Thr His Leu Asp Ala
                180                 185                 190

Leu Lys

<210> SEQ ID NO 26
<211> LENGTH: 303
<212> TYPE: PRT
<213> ORGANISM: Homo sapiens

<400> SEQUENCE: 26

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
                20                  25                  30

Ala Leu Lys Ser Val Arg Val Pro Asn Gly Gly Gly Gly Gly Gly Gly
                35                  40                  45

Leu Pro Ile Ser Thr Val Arg Glu Val Ala Leu Leu Arg Arg Leu Glu
50                  55                  60

Ala Phe Glu His Pro Asn Val Val Arg Leu Met Asp Val Cys Ala Thr
65                  70                  75                  80

Ser Arg Thr Asp Arg Glu Ile Lys Val Thr Leu Val Phe Glu His Val
                85                  90                  95

Asp Gln Asp Leu Arg Thr Tyr Leu Asp Lys Ala Pro Pro Pro Gly Leu
                100                 105                 110

Pro Ala Glu Thr Ile Lys Asp Leu Met Arg Gln Phe Leu Arg Gly Leu
                115                 120                 125

Asp Phe Leu His Ala Asn Cys Ile Val His Arg Asp Leu Lys Pro Glu
                130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
                180                 185                 190

Thr Pro Val Asp Met Trp Ser Val Gly Cys Ile Phe Ala Glu Met Phe
                195                 200                 205

Arg Arg Lys Pro Leu Phe Cys Gly Asn Ser Glu Ala Asp Gln Leu Gly
210                 215                 220

Lys Ile Phe Asp Leu Ile Gly Leu Pro Pro Glu Asp Asp Trp Pro Arg
225                 230                 235                 240

Asp Val Ser Leu Pro Arg Gly Ala Phe Pro Pro Arg Gly Pro Arg Pro
                245                 250                 255

Val Gln Ser Val Val Pro Glu Met Glu Glu Ser Gly Ala Gln Leu Leu
                260                 265                 270

Leu Glu Met Leu Thr Phe Asn Pro His Lys Arg Ile Ser Ala Phe Arg
                275                 280                 285

Ala Leu Gln His Ser Tyr Leu His Lys Asp Glu Gly Asn Pro Glu
                290                 295                 300
```

<210> SEQ ID NO 27
<211> LENGTH: 420
<212> TYPE: PRT
<213> ORGANISM: Homo sapiens

<400> SEQUENCE: 27

| Met | Ser | Gly | Arg | Pro | Arg | Thr | Thr | Ser | Phe | Ala | Glu | Ser | Cys | Lys | Pro |
|---|---|---|---|---|---|---|---|---|---|---|---|---|---|---|---|
| 1 | | | | 5 | | | | | 10 | | | | | 15 | |

Val Gln Gln Pro Ser Ala Phe Gly Ser Met Lys Val Ser Arg Asp Lys
            20                  25                  30

Asp Gly Ser Lys Val Thr Thr Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Val
    290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
            340                 345                 350

Gly Arg Asp Thr Pro Ala Leu Phe Asn Phe Thr Thr Gln Glu Leu Ser
        355                 360                 365

Ser Asn Pro Pro Leu Ala Thr Ile Leu Ile Pro Pro His Ala Arg Ile
    370                 375                 380

-continued

Gln Ala Ala Ala Ser Thr Pro Thr Asn Ala Thr Ala Ser Asp Ala
385                 390                 395                 400

Asn Thr Gly Asp Arg Gly Gln Thr Asn Asn Ala Ala Ser Ala Ser Ala
            405                 410                 415

Ser Asn Ser Thr
            420

<210> SEQ ID NO 28
<211> LENGTH: 433
<212> TYPE: PRT
<213> ORGANISM: Homo sapiens

<400> SEQUENCE: 28

Met Glu Val Val Asp Pro Gln Gln Leu Gly Met Phe Thr Glu Gly Glu
1               5                   10                  15

Leu Met Ser Val Gly Met Asp Thr Phe Ile His Arg Ile Asp Ser Thr
                20                  25                  30

Glu Val Ile Tyr Gln Pro Arg Arg Lys Arg Ala Lys Leu Ile Gly Lys
            35                  40                  45

Tyr Leu Met Gly Asp Leu Leu Gly Glu Gly Ser Tyr Gly Lys Val Lys
        50                  55                  60

Glu Val Leu Asp Ser Glu Thr Leu Cys Arg Arg Ala Val Lys Ile Leu
65                  70                  75                  80

Lys Lys Lys Lys Leu Arg Arg Ile Pro Asn Gly Glu Ala Asn Val Lys
                85                  90                  95

Lys Glu Ile Gln Leu Leu Arg Arg Leu Arg His Lys Asn Val Ile Gln
            100                 105                 110

Leu Val Asp Val Leu Tyr Asn Glu Glu Lys Gln Lys Met Tyr Met Val
        115                 120                 125

Met Glu Tyr Cys Val Cys Gly Met Gln Glu Met Leu Asp Ser Val Pro
130                 135                 140

Glu Lys Arg Phe Pro Val Cys Gln Ala His Gly Tyr Phe Cys Gln Leu
145                 150                 155                 160

Ile Asp Gly Leu Glu Tyr Leu His Ser Gln Gly Ile Val His Lys Asp
                165                 170                 175

Ile Lys Pro Gly Asn Leu Leu Leu Thr Thr Gly Gly Thr Leu Lys Ile
            180                 185                 190

Ser Asp Leu Gly Val Ala Glu Ala Leu His Pro Phe Ala Ala Asp Asp
        195                 200                 205

Thr Cys Arg Thr Ser Gln Gly Ser Pro Ala Phe Gln Pro Pro Glu Ile
210                 215                 220

Ala Asn Gly Leu Asp Thr Phe Ser Gly Phe Lys Val Asp Ile Trp Ser
225                 230                 235                 240

Ala Gly Val Thr Leu Tyr Asn Ile Thr Thr Gly Leu Tyr Pro Phe Glu
                245                 250                 255

Gly Asp Asn Ile Tyr Lys Leu Phe Glu Asn Ile Gly Lys Gly Ser Tyr
            260                 265                 270

Ala Ile Pro Gly Asp Cys Gly Pro Pro Leu Ser Asp Leu Leu Lys Gly
        275                 280                 285

Met Leu Glu Tyr Glu Pro Ala Lys Arg Phe Ser Ile Arg Gln Ile Arg
290                 295                 300

Gln His Ser Trp Phe Arg Lys Lys His Pro Pro Ala Glu Ala Pro Val
305                 310                 315                 320

Pro Ile Pro Pro Ser Pro Asp Thr Lys Asp Arg Trp Arg Ser Met Thr
                325                 330                 335

```
Val Val Pro Tyr Leu Glu Asp Leu His Gly Ala Asp Glu Asp
            340                 345                 350

Leu Phe Asp Ile Glu Asp Asp Ile Ile Tyr Thr Gln Asp Phe Thr Val
        355                 360                 365

Pro Gly Gln Val Pro Glu Glu Ala Ser His Asn Gly Gln Arg Arg
    370                 375                 380

Gly Leu Pro Lys Ala Val Cys Met Asn Gly Thr Glu Ala Ala Gln Leu
385                 390                 395                 400

Ser Thr Lys Ser Arg Ala Glu Gly Arg Ala Pro Asn Pro Ala Arg Lys
                405                 410                 415

Ala Cys Ser Ala Ser Ser Lys Ile Arg Arg Leu Ser Ala Cys Lys Gln
                420                 425                 430

Gln

<210> SEQ ID NO 29
<211> LENGTH: 487
<212> TYPE: PRT
<213> ORGANISM: Homo sapiens

<400> SEQUENCE: 29

Met Glu Thr Val Gln Leu Arg Asn Pro Pro Arg Arg Gln Leu Lys Lys
1               5                   10                  15

Leu Asp Glu Asp Ser Leu Thr Lys Gln Pro Glu Glu Val Phe Asp Val
                20                  25                  30

Leu Glu Lys Leu Gly Glu Gly Ser Tyr Gly Ser Val Tyr Lys Ala Ile
            35                  40                  45

His Lys Glu Thr Gly Gln Ile Val Ala Ile Lys Gln Val Pro Val Glu
        50                  55                  60

Ser Asp Leu Gln Glu Ile Ile Lys Glu Ile Ser Ile Met Gln Gln Cys
65                  70                  75                  80

Asp Ser Pro His Val Val Lys Tyr Tyr Gly Ser Tyr Phe Lys Asn Thr
                85                  90                  95

Asp Leu Trp Ile Val Met Glu Tyr Cys Gly Ala Gly Ser Val Ser Asp
            100                 105                 110

Ile Ile Arg Leu Arg Asn Lys Thr Leu Thr Glu Asp Glu Ile Ala Thr
        115                 120                 125

Ile Leu Gln Ser Thr Leu Lys Gly Leu Glu Tyr Leu His Phe Met Arg
    130                 135                 140

Lys Ile His Arg Asp Ile Lys Ala Gly Asn Ile Leu Leu Asn Thr Glu
145                 150                 155                 160

Gly His Ala Lys Leu Ala Asp Phe Gly Val Ala Gly Gln Leu Thr Asp
                165                 170                 175

Thr Met Ala Lys Arg Asn Thr Val Ile Gly Thr Pro Phe Trp Met Ala
            180                 185                 190

Pro Glu Val Ile Gln Glu Ile Gly Tyr Asn Cys Val Ala Asp Ile Trp
        195                 200                 205

Ser Leu Gly Ile Thr Ala Ile Glu Met Ala Glu Gly Lys Pro Pro Tyr
    210                 215                 220

Ala Asp Ile His Pro Met Arg Ala Ile Phe Met Ile Pro Thr Asn Pro
225                 230                 235                 240

Pro Pro Thr Phe Arg Lys Pro Glu Leu Trp Ser Asp Asn Phe Thr Asp
                245                 250                 255

Phe Val Lys Gln Cys Leu Val Lys Ser Pro Glu Gln Arg Ala Thr Ala
            260                 265                 270
```

```
Thr Gln Leu Leu Gln His Pro Phe Val Arg Ser Ala Lys Gly Val Ser
        275                 280                 285

Ile Leu Arg Asp Leu Ile Asn Glu Ala Met Asp Val Lys Leu Lys Arg
    290                 295                 300

Gln Glu Ser Gln Gln Arg Glu Val Asp Gln Asp Glu Glu Asn Ser
305                 310                 315                 320

Glu Glu Asp Glu Met Asp Ser Gly Thr Met Val Arg Ala Val Gly Asp
                325                 330                 335

Glu Met Gly Thr Val Arg Val Ala Ser Thr Met Thr Asp Gly Ala Asn
                340                 345                 350

Thr Met Ile Glu His Asp Asp Thr Leu Pro Ser Gln Leu Gly Thr Met
        355                 360                 365

Val Ile Asn Ala Glu Asp Glu Glu Glu Gly Thr Met Lys Arg Arg
370                 375                 380

Asp Glu Thr Met Gln Pro Ala Lys Pro Ser Phe Leu Glu Tyr Phe Glu
385                 390                 395                 400

Gln Lys Glu Lys Glu Asn Gln Ile Asn Ser Phe Gly Lys Ser Val Pro
                405                 410                 415

Gly Pro Leu Lys Asn Ser Ser Asp Trp Lys Ile Pro Asp Gly Asp
                420                 425                 430

Tyr Glu Phe Leu Lys Ser Trp Thr Val Glu Asp Leu Gln Lys Arg Leu
                435                 440                 445

Leu Ala Leu Asp Pro Met Met Glu Gln Glu Ile Glu Glu Ile Arg Gln
    450                 455                 460

Lys Tyr Gln Ser Lys Arg Gln Pro Ile Leu Asp Ala Ile Glu Ala Lys
465                 470                 475                 480

Lys Arg Arg Gln Gln Asn Phe
                485

<210> SEQ ID NO 30
<211> LENGTH: 445
<212> TYPE: PRT
<213> ORGANISM: Homo sapiens

<400> SEQUENCE: 30

Met Pro Ser Arg Ala Glu Asp Tyr Glu Val Leu Tyr Thr Ile Gly Thr
1               5                   10                  15

Gly Ser Tyr Gly Arg Cys Gln Lys Ile Arg Arg Lys Ser Asp Gly Lys
                20                  25                  30

Ile Leu Val Trp Lys Glu Leu Asp Tyr Gly Ser Met Thr Glu Ala Glu
            35                  40                  45

Lys Gln Met Leu Val Ser Glu Val Asn Leu Leu Arg Glu Leu Lys His
        50                  55                  60

Pro Asn Ile Val Arg Tyr Tyr Asp Arg Ile Ile Asp Arg Thr Asn Thr
65                  70                  75                  80

Thr Leu Tyr Ile Val Met Glu Tyr Cys Glu Gly Gly Asp Leu Ala Ser
                85                  90                  95

Val Ile Thr Lys Gly Thr Lys Glu Arg Gln Tyr Leu Asp Glu Glu Phe
                100                 105                 110

Val Leu Arg Val Met Thr Gln Leu Thr Leu Ala Leu Lys Glu Cys His
                115                 120                 125

Arg Arg Ser Asp Gly Gly His Thr Val Leu His Arg Asp Leu Lys Pro
            130                 135                 140

Ala Asn Val Phe Leu Asp Gly Lys Gln Asn Val Lys Leu Gly Asp Phe
```

```
                145                 150                 155                 160
        Gly Leu Ala Arg Ile Leu Asn His Asp Thr Ser Phe Ala Lys Thr Phe
                        165                 170                 175

Val Gly Thr Pro Tyr Tyr Met Ser Pro Glu Gln Met Asn Arg Met Ser
                        180                 185                 190

Tyr Asn Glu Lys Ser Asp Ile Trp Ser Leu Gly Cys Leu Leu Tyr Glu
                        195                 200                 205

Leu Cys Ala Leu Met Pro Pro Phe Thr Ala Phe Ser Gln Lys Glu Leu
                210                 215                 220

Ala Gly Lys Ile Arg Glu Gly Lys Phe Arg Arg Ile Pro Tyr Arg Tyr
        225                 230                 235                 240

Ser Asp Glu Leu Asn Glu Ile Ile Thr Arg Met Leu Asn Leu Lys Asp
                        245                 250                 255

Tyr His Arg Pro Ser Val Glu Glu Ile Leu Glu Asn Pro Leu Ile Ala
                        260                 265                 270

Asp Leu Val Ala Asp Glu Gln Arg Arg Asn Leu Glu Arg Arg Gly Arg
                        275                 280                 285

Gln Leu Gly Glu Pro Glu Lys Ser Gln Asp Ser Ser Pro Val Leu Ser
                290                 295                 300

Glu Leu Lys Leu Lys Glu Ile Gln Leu Gln Glu Arg Glu Arg Ala Leu
        305                 310                 315                 320

Lys Ala Arg Glu Glu Arg Leu Glu Gln Lys Glu Gln Glu Leu Cys Val
                        325                 330                 335

Arg Glu Arg Leu Ala Glu Asp Lys Leu Ala Arg Ala Glu Asn Leu Leu
                        340                 345                 350

Lys Asn Tyr Ser Leu Leu Lys Glu Arg Lys Phe Leu Ser Leu Ala Ser
                        355                 360                 365

Asn Pro Glu Leu Leu Asn Leu Pro Ser Ser Val Ile Lys Lys Lys Val
                370                 375                 380

His Phe Ser Gly Glu Ser Lys Glu Asn Ile Met Arg Ser Glu Asn Ser
        385                 390                 395                 400

Glu Ser Gln Leu Thr Ser Lys Ser Lys Cys Lys Asp Leu Lys Lys Arg
                        405                 410                 415

Leu His Ala Ala Gln Leu Arg Ala Gln Ala Leu Ser Asp Ile Glu Lys
                        420                 425                 430

Asn Tyr Gln Leu Lys Ser Arg Gln Ile Leu Gly Met Arg
                        435                 440                 445

<210> SEQ ID NO 31
<211> LENGTH: 591
<212> TYPE: PRT
<213> ORGANISM: Homo sapiens

<400> SEQUENCE: 31

Met Phe Gly Lys Arg Lys Lys Arg Val Glu Ile Ser Ala Pro Ser Asn
        1               5                   10                  15

Phe Glu His Arg Val His Thr Gly Phe Asp Gln His Glu Gln Lys Phe
                        20                  25                  30

Thr Gly Leu Pro Arg Gln Trp Gln Ser Leu Ile Glu Glu Ser Ala Arg
                        35                  40                  45

Arg Pro Lys Pro Leu Val Asp Pro Ala Cys Ile Thr Ser Ile Gln Pro
                        50                  55                  60

Gly Ala Pro Lys Thr Ile Val Arg Gly Ser Lys Gly Ala Lys Asp Gly
        65                  70                  75                  80
```

```
Ala Leu Thr Leu Leu Asp Glu Phe Glu Asn Met Ser Val Thr Arg
             85                  90                  95

Ser Asn Ser Leu Arg Arg Asp Ser Pro Pro Pro Ala Arg Ala Arg
            100                 105                 110

Gln Glu Asn Gly Met Pro Glu Glu Pro Ala Thr Thr Ala Arg Gly Gly
            115                 120                 125

Pro Gly Lys Ala Gly Ser Arg Gly Arg Phe Ala Gly His Ser Glu Ala
            130                 135                 140

Gly Gly Gly Ser Gly Asp Arg Arg Arg Ala Gly Pro Glu Lys Arg Pro
145             150                 155                 160

Lys Ser Ser Arg Glu Gly Ser Gly Gly Pro Gln Glu Ser Ser Arg Asp
                165                 170                 175

Lys Arg Pro Leu Ser Gly Pro Asp Val Gly Thr Pro Gln Pro Ala Gly
            180                 185                 190

Leu Ala Ser Gly Ala Lys Leu Ala Ala Gly Arg Pro Phe Asn Thr Tyr
            195                 200                 205

Pro Arg Ala Asp Thr Asp His Pro Ser Arg Gly Ala Gln Gly Glu Pro
            210                 215                 220

His Asp Val Ala Pro Asn Gly Pro Ser Ala Gly Gly Leu Ala Ile Pro
225             230                 235                 240

Gln Ser Ser Ser Ser Ser Arg Pro Pro Thr Arg Ala Arg Gly Ala
                245                 250                 255

Pro Ser Pro Gly Val Leu Gly Pro His Ala Ser Glu Pro Gln Leu Ala
            260                 265                 270

Pro Pro Ala Cys Thr Pro Ala Ala Pro Ala Val Pro Gly Pro Pro Gly
            275                 280                 285

Pro Arg Ser Pro Gln Arg Glu Pro Gln Arg Val Ser His Glu Gln Phe
            290                 295                 300

Arg Ala Ala Leu Gln Leu Val Val Asp Pro Gly Asp Pro Arg Ser Tyr
305             310                 315                 320

Leu Asp Asn Phe Ile Lys Ile Gly Glu Gly Ser Thr Gly Ile Val Cys
            325                 330                 335

Ile Ala Thr Val Arg Ser Ser Gly Lys Leu Val Ala Val Lys Lys Met
            340                 345                 350

Asp Leu Arg Lys Gln Gln Arg Arg Glu Leu Leu Phe Asn Glu Val Val
            355                 360                 365

Ile Met Arg Asp Tyr Gln His Glu Asn Val Val Glu Met Tyr Asn Ser
            370                 375                 380

Tyr Leu Val Gly Asp Glu Leu Trp Val Val Met Glu Phe Leu Glu Gly
385             390                 395                 400

Gly Ala Leu Thr Asp Ile Val Thr His Thr Arg Met Asn Glu Glu Gln
            405                 410                 415

Ile Ala Ala Val Cys Leu Ala Val Leu Gln Ala Leu Ser Val Leu His
            420                 425                 430

Ala Gln Gly Val Ile His Arg Asp Ile Lys Ser Asp Ser Ile Leu Leu
            435                 440                 445

Thr His Asp Gly Arg Val Lys Leu Ser Asp Phe Gly Phe Cys Ala Gln
            450                 455                 460

Val Ser Lys Glu Val Pro Arg Arg Lys Ser Leu Val Gly Thr Pro Tyr
465             470                 475                 480

Trp Met Ala Pro Glu Leu Ile Ser Arg Leu Pro Tyr Gly Pro Glu Val
                485                 490                 495

Asp Ile Trp Ser Leu Gly Ile Met Val Ile Glu Met Val Asp Gly Glu
```

```
                500                 505                 510
Pro Pro Tyr Phe Asn Glu Pro Pro Leu Lys Ala Met Lys Met Ile Arg
        515                 520                 525

Asp Asn Leu Pro Pro Arg Leu Lys Asn Leu His Lys Val Ser Pro Ser
        530                 535                 540

Leu Lys Gly Phe Leu Asp Arg Leu Leu Val Arg Asp Pro Ala Gln Arg
545                 550                 555                 560

Ala Thr Ala Ala Glu Leu Leu Lys His Pro Phe Leu Ala Lys Ala Gly
                565                 570                 575

Pro Pro Ala Ser Ile Val Pro Leu Met Arg Gln Asn Arg Thr Arg
        580                 585                 590
```

<210> SEQ ID NO 32
<211> LENGTH: 671
<212> TYPE: PRT
<213> ORGANISM: Homo sapiens

<400> SEQUENCE: 32

```
Met Ala Asp Pro Ala Gly Pro Pro Ser Glu Gly Glu Glu Ser
1               5                   10                  15

Thr Val Arg Phe Ala Arg Lys Gly Ala Leu Arg Gln Lys Asn Val His
            20                  25                  30

Glu Val Lys Asn His Lys Phe Thr Ala Arg Phe Phe Lys Gln Pro Thr
        35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Ala Ser Asp
                85                  90                  95

Asp Pro Arg Ser Lys His Lys Phe Lys Ile His Thr Tyr Ser Ser Pro
            100                 105                 110

Thr Phe Cys Asp His Cys Gly Ser Leu Leu Tyr Gly Leu Ile His Gln
        115                 120                 125

Gly Met Lys Cys Asp Thr Cys Met Met Asn Val His Lys Arg Cys Val
    130                 135                 140

Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
                165                 170                 175

Val Arg Asp Ala Lys Asn Leu Val Pro Met Asp Pro Asn Gly Leu Ser
            180                 185                 190

Asp Pro Tyr Val Lys Leu Lys Leu Ile Pro Asp Pro Lys Ser Glu Ser
        195                 200                 205

Lys Gln Lys Thr Lys Thr Ile Lys Cys Ser Leu Asn Pro Glu Trp Asn
    210                 215                 220

Glu Thr Phe Arg Phe Gln Leu Lys Glu Ser Asp Lys Asp Arg Arg Leu
225                 230                 235                 240

Ser Val Glu Ile Trp Asp Trp Asp Leu Thr Ser Arg Asn Asp Phe Met
                245                 250                 255

Gly Ser Leu Ser Phe Gly Ile Ser Glu Leu Gln Lys Ala Ser Val Asp
            260                 265                 270

Gly Trp Phe Lys Leu Leu Ser Gln Glu Glu Gly Glu Tyr Phe Asn Val
        275                 280                 285
```

```
Pro Val Pro Pro Glu Gly Ser Glu Ala Asn Glu Glu Leu Arg Gln Lys
    290                 295                 300

Phe Glu Arg Ala Lys Ile Ser Gln Gly Thr Lys Val Pro Glu Glu Lys
305                 310                 315                 320

Thr Thr Asn Thr Val Ser Lys Phe Asp Asn Asn Gly Asn Arg Asp Arg
                325                 330                 335

Met Lys Leu Thr Asp Phe Asn Phe Leu Met Val Leu Gly Lys Gly Ser
                340                 345                 350

Phe Gly Lys Val Met Leu Ser Glu Arg Lys Gly Thr Asp Glu Leu Tyr
            355                 360                 365

Ala Val Lys Ile Leu Lys Lys Asp Val Val Ile Gln Asp Asp Asp Val
        370                 375                 380

Glu Cys Thr Met Val Glu Lys Arg Val Leu Ala Leu Pro Gly Lys Pro
385                 390                 395                 400

Pro Phe Leu Thr Gln Leu His Ser Cys Phe Gln Thr Met Asp Arg Leu
                405                 410                 415

Tyr Phe Val Met Glu Tyr Val Asn Gly Gly Asp Leu Met Tyr His Ile
                420                 425                 430

Gln Gln Val Gly Arg Phe Lys Glu Pro His Ala Val Phe Tyr Ala Ala
            435                 440                 445

Glu Ile Ala Ile Gly Leu Phe Phe Leu Gln Ser Lys Gly Ile Ile Tyr
        450                 455                 460

Arg Asp Leu Lys Leu Asp Asn Val Met Leu Asp Ser Glu Gly His Ile
465                 470                 475                 480

Lys Ile Ala Asp Phe Gly Met Cys Lys Glu Asn Ile Trp Asp Gly Val
                485                 490                 495

Thr Thr Lys Thr Phe Cys Gly Thr Pro Asp Tyr Ile Ala Pro Glu Ile
                500                 505                 510

Ile Ala Tyr Gln Pro Tyr Gly Lys Ser Val Asp Trp Trp Ala Phe Gly
            515                 520                 525

Val Leu Leu Tyr Glu Met Leu Ala Gly Gln Ala Pro Phe Glu Gly Glu
        530                 535                 540

Asp Glu Asp Glu Leu Phe Gln Ser Ile Met Glu His Asn Val Ala Tyr
545                 550                 555                 560

Pro Lys Ser Met Ser Lys Glu Ala Val Ala Ile Cys Lys Gly Leu Met
                565                 570                 575

Thr Lys His Pro Gly Lys Arg Leu Gly Cys Gly Pro Glu Gly Glu Arg
                580                 585                 590

Asp Ile Lys Glu His Ala Phe Phe Arg Tyr Ile Asp Trp Glu Lys Leu
            595                 600                 605

Glu Arg Lys Glu Ile Gln Pro Pro Tyr Lys Pro Lys Ala Arg Asp Lys
        610                 615                 620

Arg Asp Thr Ser Asn Phe Asp Lys Glu Phe Thr Arg Gln Pro Val Glu
625                 630                 635                 640

Leu Thr Pro Thr Asp Lys Leu Phe Ile Met Asn Leu Asp Gln Asn Glu
                645                 650                 655

Phe Ala Gly Phe Ser Tyr Thr Asn Pro Glu Phe Val Ile Asn Val
                660                 665                 670
```

<210> SEQ ID NO 33
<211> LENGTH: 525
<212> TYPE: PRT
<213> ORGANISM: Homo sapiens

<400> SEQUENCE: 33

-continued

```
Met Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
            20                  25                  30

Asp Gln Pro Glu Asp Ala Gly Ser Glu Asp Leu Glu Glu Gly Gly
        35                  40                  45

Gln Leu Asn Glu Ser Met Asp His Gly Gly Val Gly Pro Tyr Glu Leu
    50                  55                  60

Gly Met Glu His Cys Glu Lys Phe Glu Ile Ser Glu Thr Ser Val Asn
65                  70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110

Gly Ala Asn Thr Gly Lys Ile Phe Ala Met Lys Val Leu Lys Lys Ala
            115                 120                 125

Met Ile Val Arg Asn Ala Lys Asp Thr Ala His Thr Lys Ala Glu Arg
130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
            165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
            195                 200                 205

Leu His Gln Lys Gly Ile Ile Tyr Arg Asp Leu Lys Pro Glu Asn Ile
210                 215                 220

Met Leu Asn His Gln Gly His Val Lys Leu Thr Asp Phe Gly Leu Cys
225                 230                 235                 240

Lys Glu Ser Ile His Asp Gly Thr Val Thr His Thr Phe Cys Gly Thr
                245                 250                 255

Ile Glu Tyr Met Ala Pro Glu Ile Leu Met Arg Ser Gly His Asn Arg
            260                 265                 270

Ala Val Asp Trp Trp Ser Leu Gly Ala Leu Met Tyr Asp Met Leu Thr
            275                 280                 285

Gly Ala Pro Pro Phe Thr Gly Glu Asn Arg Lys Lys Thr Ile Asp Lys
            290                 295                 300

Ile Leu Lys Cys Lys Leu Asn Leu Pro Pro Tyr Leu Thr Gln Glu Ala
305                 310                 315                 320

Arg Asp Leu Leu Lys Lys Leu Leu Lys Arg Asn Ala Ala Ser Arg Leu
                325                 330                 335

Gly Ala Gly Pro Gly Asp Ala Gly Glu Val Gln Ala His Pro Phe Phe
            340                 345                 350

Arg His Ile Asn Trp Glu Glu Leu Ala Arg Lys Val Glu Pro Pro
            355                 360                 365

Phe Lys Pro Leu Leu Gln Ser Glu Glu Asp Val Ser Gln Phe Asp Ser
            370                 375                 380

Lys Phe Thr Arg Gln Thr Pro Val Asp Ser Pro Asp Asp Ser Thr Leu
385                 390                 395                 400

Ser Glu Ser Ala Asn Gln Val Phe Leu Gly Phe Thr Tyr Val Ala Pro
                405                 410                 415
```

```
Ser Val Leu Glu Ser Val Lys Glu Lys Phe Ser Phe Glu Pro Lys Ile
            420                 425                 430

Arg Ser Pro Arg Arg Phe Ile Gly Ser Pro Arg Thr Pro Val Ser Pro
        435                 440                 445

Val Lys Phe Ser Pro Gly Asp Phe Trp Gly Arg Gly Ala Ser Ala Ser
    450                 455                 460

Thr Ala Asn Pro Gln Thr Pro Val Glu Tyr Pro Met Glu Thr Ser Gly
465                 470                 475                 480

Ile Glu Gln Met Asp Val Thr Met Ser Gly Glu Ala Ser Ala Pro Leu
                485                 490                 495

Pro Ile Arg Gln Pro Asn Ser Gly Pro Tyr Lys Lys Gln Ala Phe Pro
            500                 505                 510

Met Ile Ser Lys Arg Pro Glu His Leu Arg Met Asn Leu
            515                 520                 525

<210> SEQ ID NO 34
<211> LENGTH: 396
<212> TYPE: PRT
<213> ORGANISM: Homo sapiens

<400> SEQUENCE: 34

Met Pro Arg Val Lys Ala Ala Gln Ala Gly Arg Gln Ser Ser Ala Lys
1               5                   10                  15

Arg His Leu Ala Glu Gln Phe Ala Val Gly Glu Ile Ile Thr Asp Met
                20                  25                  30

Ala Lys Lys Glu Trp Lys Val Gly Leu Pro Ile Gly Gln Gly Gly Phe
            35                  40                  45

Gly Cys Ile Tyr Leu Ala Asp Met Asn Ser Ser Glu Ser Val Gly Ser
    50                  55                  60

Asp Ala Pro Cys Val Val Lys Val Glu Pro Ser Asp Asn Gly Pro Leu
65                  70                  75                  80

Phe Thr Glu Leu Lys Phe Tyr Gln Arg Ala Ala Lys Pro Glu Gln Ile
                85                  90                  95

Gln Lys Trp Ile Arg Thr Arg Lys Leu Lys Tyr Leu Gly Val Pro Lys
            100                 105                 110

Tyr Trp Gly Ser Gly Leu His Asp Lys Asn Gly Lys Ser Tyr Arg Phe
    115                 120                 125

Met Ile Met Asp Arg Phe Gly Ser Asp Leu Gln Lys Ile Tyr Glu Ala
130                 135                 140

Asn Ala Lys Arg Phe Ser Arg Lys Thr Val Leu Gln Leu Ser Leu Arg
145                 150                 155                 160

Ile Leu Asp Ile Leu Glu Tyr Ile His Glu His Glu Tyr Val His Gly
                165                 170                 175

Asp Ile Lys Ala Ser Asn Leu Leu Leu Asn Tyr Lys Asn Pro Asp Gln
            180                 185                 190

Val Tyr Leu Val Asp Tyr Gly Leu Ala Tyr Arg Tyr Cys Pro Glu Gly
    195                 200                 205

Val His Lys Glu Tyr Lys Glu Asp Pro Lys Arg Cys His Asp Gly Thr
210                 215                 220

Ile Glu Phe Thr Ser Ile Asp Ala His Asn Gly Val Ala Pro Ser Arg
225                 230                 235                 240

Arg Gly Asp Leu Glu Ile Leu Gly Tyr Cys Met Ile Gln Trp Leu Thr
                245                 250                 255

Gly His Leu Pro Trp Glu Asp Asn Leu Lys Asp Pro Lys Tyr Val Arg
            260                 265                 270
```

```
Asp Ser Lys Ile Arg Tyr Arg Glu Asn Ile Ala Ser Leu Met Asp Lys
    275                 280                 285

Cys Phe Pro Glu Lys Asn Lys Pro Gly Glu Ile Ala Lys Tyr Met Glu
    290                 295                 300

Thr Val Lys Leu Leu Asp Tyr Thr Glu Lys Pro Leu Tyr Glu Asn Leu
305                 310                 315                 320

Arg Asp Ile Leu Leu Gln Gly Leu Lys Ala Ile Gly Ser Lys Asp Asp
                325                 330                 335

Gly Lys Leu Asp Leu Ser Val Val Glu Asn Gly Gly Leu Lys Ala Lys
                340                 345                 350

Thr Ile Thr Lys Lys Arg Lys Lys Glu Ile Glu Glu Ser Lys Glu Pro
            355                 360                 365

Gly Val Glu Asp Thr Glu Trp Ser Asn Thr Gln Thr Glu Glu Ala Ile
    370                 375                 380

Gln Thr Arg Ser Arg Thr Arg Lys Arg Val Gln Lys
385                 390                 395
```

FULL LENGTH KINASE ACTIVITY-CONFORMATION REPORTER

REFERENCE TO A SEQUENCE LISTING SUBMITTED ON COMPUTER

The content of the ASCII text file of the sequence listing named 16785-215_seq_ST25, which was filed in International Patent Application No. PCT/EP2017/074761, on Sep. 29, 2017, downloaded from the WIPO database, is 152 kb in size with a created date of Sep. 29, 2017, and electronically submitted via EFS-Web herewith the application, is incorporated herein by reference in its entirety.

The invention relates to a protein kinase reporter, a polynucleotide and a cell for an intramolecular protein-fragment complementation assay (PCA) as well as a method of conducting such an assay.

BACKGROUND OF THE INVENTION

Figure 1:
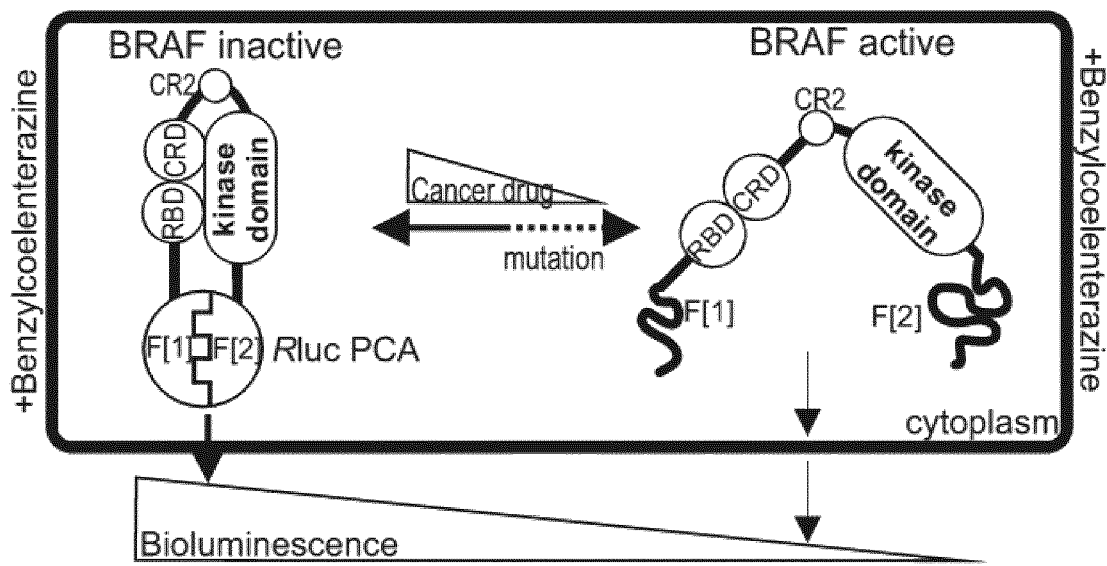

Small molecule protein kinase inhibitors are among the most intensively pursued class of anti-cancer therapeutics. The reasons are that protein kinases adopt central roles in proliferative signal transmission and that kinases contain a highly conserved ATP-binding pocket that can be selectively targeted by synthetic chemical lead compounds (Knighton, D. R. et al. Crystal structure of the catalytic subunit of cyclic adenosine monophosphate-dependent protein kinase. *Science* 253, 407-414 (1991), Fleuren, E. D., Zhang, L., Wu, J. & Daly, R. J. The kinome 'at large' in cancer. *Nat Rev Cancer* 16, 83-98 (2016)). The oncogenic potential of kinases is dependent on constitutive kinase activity which is essential for survival and proliferation of the cancer cell. Besides deregulation of upstream pathways, defined mutations are sufficient to convert the kinase to a cancer driver which is susceptible to the appropriate kinase inhibitor. The RAS-RAF-MEK-ERK pathway is one frequently targeted signaling cascade which is hyper-activated in several tumors showing mutations in the Ras-GTPase, Raf-kinase and to a lesser extend also in the Mek1/2 genes. The acronyms RAS and RAF were originally based on "rat sarcoma" and "rapidly accelerated fibrosarcoma". However, these acronyms are now well established to designate the respective protein (families). The ARAF, BRAF, and CRAF kinases are the upstream regulators of mitogen-activated protein kinase (MAP kinase, MAPK) signaling (Desideri, E., Cavallo, A. L. & Baccarini, M. Alike but Different: RAF Paralogs and Their Signaling Outputs. *Cell* 161, 967-970 (2015)). The acronym MEK derives from MAPK/ERK kinase and relates to the MAP kinases MEK1 and MEK2. They are amongst others direct targets for RAF phosphorylation (Caunt, C. J. et al. MEK1 and MEK2 inhibitors and cancer therapy: the long and winding road. *Nat Rev Cancer* 10, 577-592 (2015)). In the absence of a stimulus the RAF kinase adopts a closed conformation, the N terminus inhibits the kinase activity localized at the C terminus (FIG. 1). Under physiological conditions RAF activation depends on protein-protein interactions (PPIs) with GTP-bound RAS via the RAS binding domain (RBD) of RAF. Activated GTP-bound RAS recruits cytoplasmic RAF to the membrane and initiates the shift to the open and active kinase conformation. This is triggered by alterations of the RAF kinase phosphorylation status leading to disruption of the auto-inhibitory RAF configuration (Lavoie, H. & Therrien, M. Regulation of RAF protein kinases in ERK signaling. *Nat Rev Mol Cell Biol* 16, 281-298 (2015)). Under pathological conditions RAF mutants adopt a constitutively active kinase confor-mation (open conformation). One member of the RAF family, BRAF, is the most frequently mutated oncogene in the kinase superfamily (Fleuren, E. D., Zhang, L., Wu, J. & Daly, R. J. The kinome 'at large' in cancer. *Nat Rev Cancer* 16, 83-98 (2016); Davies, H. et al. Mutations of the BRAF gene in human cancer. *Nature* 417, 949-954 (2002)). The most common gain of function mutations in BRAF is the substitution V600E which is found in around 60% of all melanomas (Lito, P., Rosen, N. & Solit, D. B. Tumor adaptation and resistance to RAF inhibitors. Nature medicine 19, 1401-1409 (2013)). It is believed that the amino acid exchange V600E serves as phospho-mimetic substitution in the BRAF kinase domain which creates a catalytically active BRAF (open conformation) representing one of the most recurrent oncogenic human disease mutations. Selective inhibitors of BRAF-V600E (vemurafenib, dabrafenib) have been approved for the treatment of metastatic melanoma which express BRAF-V600E showing profound clinical responses in patients (Lito, P., Rosen, N. & Solit, D. B. Tumor adaptation and resistance to RAF inhibitors. *Nat med* 19, 1401-1409 (2013), Girotti, M. R., Saturno, G., Lorigan, P. & Marais, R. No longer an untreatable disease: how targeted and immunotherapies have changed the management of melanoma patients. *Molecular oncology* 8, 1140-1158 (2014)). Other BRAF inhibitors (BRAFi) such as encorafenib and PLX8394 are in clinical trials (Zhang, C. et al. RAF inhibitors that evade paradoxical MAPK pathway activation. *Nature* 526, 583-586 (2015); Adelmann, C. H. et al. Comparative profiles of BRAF inhibitors: the paradox index as a predictor of clinical toxicity. *Oncotarget* (2016)). However, the duration of the anti-tumor response is variable and the efficacies of BRAFi are limited through the onset of drug resistance. What complicates the analyses of RAF kinase drug efficacies is that a collection of additional oncogenic mutations has been identified in BRAF and CRAF. The mechanism of action is not fully understood but it is assumed that it is related to alterations of the closed conformation, to dimerization enhancement of the kinase domain and to the mimicking of phosphorylation. In addition to cancer also other human disorders are associated with BRAF and CRAF mutations; example are RASopathies such as the Noonan syndrome and the Leopard syndrome (Lavoie, H. & Therrien, M. Regulation of RAF protein kinases in ERK signaling. *Nat Rev Mol Cell Biol* 16, 281-298 (2015)). Active RAF directly phosphorylates and activates MEK1 or MEK2 which are dual specific kinases that in turn activate ERK (extracellular signal-regulated kinases). Compared to RAF the MEK kinases are much smaller but nevertheless they contain a N-terminal regulatory region that stabilizes the inactive kinase conformation (=negative regulatory region). Cancer/disease inducing mutations of MEK are for example found in the regulatory region. Cancer cells that contain either activating RAF or RAS mutations are sensitive to MEK inhibitors (MEKi). MEK1 and MEK 2 are the only activators of ERK, the effector kinases of the RAS-RAF-MEK-ERK pathway. MEK kinases serve therefore as ERK1 and ERK2 gate-keeper kinases. Although cancer mutations are rare in MEK this dual kinase has become a central cancer drug target (Caunt, C. J. et al. MEK1 and MEK2 inhibitors and cancer therapy: the long and winding road. *Nat Rev Cancer* 10, 577-592 (2015)). Recently drug combinations of RAF and MEK inhibitors showed a clear benefit in efficacy and tolerability in treating BRAF-V600E melanoma in clinical phase III trials (Caunt, C. J. et al. MEK1 and MEK2 inhibitors and cancer therapy: the long and winding road. *Nat Rev Cancer* 10, 577-592 (2015); Robert C, Improved overall survival in melanoma with combined dabrafenib and trametinib, *N Engl J Med,* 1, 30-39 (2015)).

The complexities of RAF regulation, RAF-MEK-ERK signaling, and RAF and MEK activation are longing for new means to survey kinase activities and conformations in normal and pathophysiological conditions. There is a need to systematically track modes of drug: kinase interactions which would have benefits for the understanding of temporal drug efficacies, drug resistance mechanism, and off-target effects. Either mutations, kinase inhibitors or combinations of both change the activity conformation. Tracking the rearrangement of auto-inhibited kinase domain conformations would ease to solve (i) the mode of kinase activity regulation and (ii) would provide new means to screen for ATP-competitive or allosteric kinase inhibitors. Conventionally, RAF or MEK kinase activity measurements are either performed in vitro or indirectly by the quantification of downstream readouts (MAPK substrate phosphorylation). Non-invasive cell-based reporter assays for systematically studying the regulation, mode of action, and inhibition of RAF and MEK isoforms and different cancerogenic kinase mutants are missing.

DESCRIPTION OF THE INVENTION

The present invention provides a reporter for an intramolecular protein-fragment complementation assay characterized in that the reporter is a fused protein comprising a first fragment, a second fragment and a protein kinase sequence section, wherein the first fragment and the second fragment are derived from different sections of the same split protein, wherein the kinase sequence section intervenes between the first fragment and the second fragment and wherein kinase sequence section comprises a kinase domain sequence and one or more regulatory sequence(s).

The reporter according to the invention is a fused protein construct which enables an intramolecular protein-fragment complementation assay (PCA). The engineered construct may be encoded by a polynucleotide and expressed in transient as well as stable cell lines. Thus, the fused reporter enables conducting a method for quantifying drug-induced kinase inactivation in a cell-based bioluminescence assay. The general concept of a PCA is for example described in EP 0 966 685 B1. According to the PCA strategy a molecular interaction, i.e. the special contact between two proteins can be investigated by fusing the potentially interacting partners to different sections of a so-called split protein. In literature, the split protein, from which protein the fragments are derived, may also be referred to as reporter protein. A reporting signal results from assembly of the fragments in case the contact of the interacting partners is established. If the interaction between the two fragments is established a functional unit is achieved. For example the fragments may be luciferase fragments and the assembled functional luciferase enzyme produces a bioluminescence signal upon oxidation of a substrate.

In the present invention the reporter protein is a reporter for an intramolecular interaction. The concept of an intramolecular PCA system has been used before for assaying conformational changes, e.g. U.S. Pat. No. 8,178,654 B2 describes an estrogen receptor system. In such intramolecular PCA systems, both PCA fragments are part of one construct. The reporter according to the invention is a single protein that includes two fragments of a split protein, for example a first and a second fragment of a luciferase protein. The two different fragments are located at the terminal parts of the reporter sequence and a protein kinase sequence is located between them. The concept of the assay relying on the kinase reporter is exemplarily shown in FIG. 1. The auto-inhibited state of a reporter including a wild type BRAF sequence has a closed, inactive conformation. In this conformation, the two terminal fragments F[1] and [F2] of the reporter arrange to form a functional unit. In contrast, the active state showing kinase activity is a so-called open state, wherein the N-terminal regulatory domains are detached from the kinase domain and allow the kinase to interact with the substrate. In this alternative conformation, the condition of close contact, which is a prerequisite for a signal associated with the split protein is not given. The inventors found that the reporter with luciferase based fragments may be expressed in cells and allows to quantify conformational changes of RAF kinases directly in the living cell. In contrast to the wild type, a reporter based on a BRAF-V600E sequence did show a reduced bioluminescence measured in relative luminescence units (RLU). This reflects that the BRAF-V600E mutant, which is constitutively active, is mainly present in an open conformation. In a similar way the inventors constructed MEK kinase reporters, wherein site-directed mutations at the RAF kinase phosphorylation sites in MEK1/2 did show a lower RLU signal. Thus, also here the constitutively active kinase sequence of MEK shows the open conformation.

The RAF reporter proofed valuable to investigate the specific effect of kinase inhibitors such as vemurafenib, encorafenib, dabrafenib, and PLX8394 on the RAF conformation in the cellular context. A time and concentration dependent increase of the luminescence signal could be observed for the reporter with the drug-susceptible RAF protein sequence (V600E), whereas the wild type based reporter was not affected. Thus, the reporter allows the monitoring of drug-induced conformational changes in a cell-based assay and this in a time and dose dependent manner. These results go along with the theory that the cancer drugs shift the conformation towards a closed state similar to the auto-inhibited conformation. Additionally, distinct stable cell lines expressing the reporter have been generated. They can give access to in vivo models with an implemented RAF kinase reporter, such as experiments in living tumour mouse models. A proof-of-principle experiment for PCA assays and on line investigation of small molecule influence was given by protein kinase A (PKA) PCA luciferase measurements in living mice and zebrafish embryos (Röck, R. et al. In-vivo detection of binary PKA network interactions upon activation of endogenous GPCRs. *Scientific reports* 5, 11133 (2015)). The results of the present study underline that the non-invasive cell-based reporter assays can be used to systematically study the regulation, mode of action, and inhibition of wildtype and mutated RAF isoforms. It is this the first implementation of a full length RAF kinase reporter platform to record kinase conformations/activities and drug efficacies directly in the living cell.

The term "protein kinase sequence section" may refer to a protein sequence derived from a protein with kinase activity towards proteins (i.e. a protein kinase). The sequence section preferably is a sequence section corresponding to the full length protein kinase, thus including a catalytic kinase domain as well as other sequence section(s).

A "regulatory sequence" may be any part of a protein kinase sequence, which is not part of the catalytic kinase domain. The regulatory sequence(s) may be independently selected from the group consisting of a sequence for a domain associated with auto-inhibition of the kinase, a negative regulatory region or another sequence section of yet unknown mechanism. It may be located N-terminally or C-terminally to the kinase domain. In one embodiment, the at least one regulatory sequence is located N-terminally to the kinase domain. Especially in the context of the present invention, the protein kinase sequence section is derived from a protein kinases known to or suspected to have an intramolecular auto-inhibitory mechanism associated with a conformational change. Preferably, the kinase sequence section is derived from a protein kinase known to have an intra-molecular auto-inhibitory mechanism associated with a conformation change of the protein kinase, i.e. the regulatory sequence section is an auto-inhibitory sequence. The inventors also investigated kinase reporters with PI3K (phosphatidylinositol-3-kinase) or protein kinase A (PKA) as kinase sequence section and the fragments were derived from *Renilla* luciferase. These reporters were not successful in exhibiting a PCA signal (data not shown). For these kinases, it is assumed that the inhibitory mechanism involves binary interactions with regulatory and phosphotransferase inactivating subunits; i.e. an alternative mechanism to the intramolecular auto-inhibitory interaction of RAF and MEK1/2. Besides RAF kinases and MEK1/2, further protein kinases are suspected to have a mainly intramolecular auto-inhibition mechanism associated with a conformational change. These are for example further kinases of the RAS-RAF-ERK pathway, kinases of the pathways activating p38 MAPK and JNK (c-Jun N-terminal) MAPK, AMP-activated kinases, NEK1-10, JAK, MST, 21-activated kinases (PAK), SRC and SRC-related kinases. The reporter according to the invention may also be suitable to investigate if a protein kinase shows an intramolecular auto-inhibition mechanism. A selection of kinase sequences showed a detectable luminescence signal when being provided in a reporter construct according to the invention. Thus, the concept of the present invention is not limited to kinases involved in the mitogen-activated protein kinase (MAPK) signaling pathway. In one embodiment, the kinase sequence section preferably is a full-length sequence of a kinase selected from the group consisting of SEQ ID No: 25 to 34.

In a preferred embodiment, the kinase sequence section is a full-length sequence of a kinase involved in the mitogen-activated protein kinase (MAPK) signaling pathway, thus especially those kinases involved in regulating MAP kinases, such as those kinases involved in activation of ERK1/2 (kinases of the RAS-RAF-ERK pathway). Especially, the invention refers to reporters wherein the protein kinase sequence section is a MAP kinase kinase kinase (MAP3K, MAPKKK) or a MAP kinase kinase (MAP2K, MAPKK).

For example, in a preferred embodiment, the protein kinase sequence section comprised in the reporter is selected out of the group consisting of a RAF protein sequence and a MEK protein, preferably a RAF protein sequence.

The term "RAF protein sequence" as used according to the invention refers to protein sequence for a protein from a family of MAP3K kinases including ARAF (or ARaf, A-Raf, SEQ ID No: 1), BRAF (or BRaf, B-Raf, SEQ ID No: 2), and CRAF (or CRAF, C-Raf, Raf-1, v-Raf, SEQ ID No: 3) with their isoforms and mutations. This includes the constantly growing collection of RAF mutations which deregulate RAF signaling such as the amino acid substitutions in BRAF-V600E (SEQ ID No: 5), BRAF-K601E (SEQ ID No: 10) and generally modifications of distinct amino acids in the regions of BRAF 464-472 and 580-618. Other examples for activating mutations are CRAF-S257L (SEQ ID No: 11), CRAF-S259A (SEQ ID No: 12), and ARAF-S214C (SEQ ID No: 4). It is expected that the method allows a sequence variability regarding the RAF protein sequences comprised in the constructs. Thus, up to 5% of the sequence of the RAF protein may differ from the native human sequences. This may allow investigating also the proteins of other species. Functional motives may be identified with the method of the invention and should be preferably conserved to study other effects of sequence variability.

Thus, in one embodiment, the RAF protein sequence has a sequence identity of at least 95% to a sequence selected out of the group consisting of SEQ ID No: 1 to 3. Moreover, it may be preferred that the RAF protein sequence has a sequence identity of at least 98% to a sequence selected out of the group comprising SEQ ID No: 1 to SEQ ID No 12. Preferably, the RAF protein sequence has a sequence selected out of the group consisting of SEQ ID No: 1 to SEQ ID No: 12, preferably SEQ ID No: 2, 5, 6, 7, 8 and 9.

Especially, the BRAF sequence and therein the ones with oncogenic mutation V600E are preferred due to their pathological importance. Thus, in a preferred embodiment the reporter comprises the sequence of full-length BRAF with SEQ ID No: 2 or its mutants BRAF(V600E) with SEQ ID No: 5, BRAF(V600K) with SEQ ID No: 6, BRAF(V600R) with SEQ ID No: 7, BRAF(D549G) with SEQ ID No: 8 and BRAF(G469A) with SEQ ID No: 9, preferably BRAF V600E (SEQ ID No: 5).

In another embodiment the kinase reporter comprises a MEK protein sequence. The term "MEK protein sequence" as used according to the invention refers to protein sequence for a protein from a family of MAP2K or MAPKK kinases including MEK1 (SEQ ID No: 13) and MEK2 (SEQ ID No: 14). A sequence variability of 5% is acceptable for the same reasons as for the RAF protein. Besides the wild-type sequence, the inventors investigated MEK2 sequences with mutations at S218 and/or S222 which are the phosphorylation sites for RAF. SEQ ID No: 15 comprising a S218A mutation and represents a mutation that may be considered as inert towards activation by phosphorylation, e.g. by RAF. SEQ ID No: 16 includes the double mutation S218E/S222E. The glutamate residues are considered as surrogates for an activation by phosphorylation. Accordingly, this activated MEK1 sequences exhibits a lower luminescence signal (shift towards active open conformation).

In one embodiment, the MEK protein sequence has a sequence identity of at least 95% to a sequence selected out of the group consisting of SEQ ID No: 13 and SEQ ID No: 14. Moreover, it may be preferred that the MEK protein sequence has a sequence identity of at least 98% to a sequence selected out of the group comprising SEQ ID No: 13 to SEQ ID No 16. Preferably, the MEK protein sequence has a sequence selected out of the group consisting of SEQ ID No: 13 to SEQ ID No: 16, preferably SEQ ID No: 13 and 16.

The term "fragment" as used according to the invention refers to a sequence section derived from a protein suitable to give an appropriate signal for readout. The two fragments comprise sequences from different sections of a split protein. To obtain the fragments the native sequence of a protein that gives a signal for an assay read-out is split up. Various proteins can be split into two parts and reconstitute non-covalently. Known split proteins for deriving fragments suitable in PCA are for example β-lactamase, dihydrofolate reductase (DHFR), focal adhesion kinase (FAK), Gal4, GFP (split-GFP), e.g. EGFP (enhanced green fluorescent protein) and IFP (increased fluorescent protein), horseradish peroxidase, infrared fluorescent protein IFP1.4, β-galactosidase (LacZ), luciferase, tobacco etch virus protease (TEV), and ubiquitin. Depending on the split protein the read-out of a signal may be colorimetric or fluorometric. Often the reconstituted split protein is an enzyme catalyzing formation of a detectable product when an appropriate substrate is provided. Alternatively, the complementation might be detected with a labeled ligand binding (e.g. Fluorescein-conjugated methotrexate fMTX as ligand for DHFR), In case of a fluorescent split protein (e.g. split GFP), the reconstituted split protein itself is detectable. This variant is also referred to as bimolecular fluorescence complementation. Alternative to an optical read-out, the fragment complementation may be detected by clonal selection, when the complemented split protein provides an essential function for survival of the cells expressing the reporter. This method may be for example applied for a DHFR-based complementation assay in DHFR deficient cells. These cells can only grow on a nucleotide free medium, when the conditions for complementation of the DHFR-PCA fragments are met (Remy, I.; Michnick, S. W., Clonal selection and in vivo quantitation of protein interactions with protein-fragment complementation assays. *Proc Natl Acad Sci USA*. 96, 5394-5399 (1999)). An overview of PCA techniques and potential split proteins is for example given in the review by Michnick et al. (Michnick S. W, Ear P. H., Manderson E. N., Remy I., Stefan E., Universal strategies in research and drug discovery based on protein-fragment complementation assays. *Nat Rev Drug Discov* 7, 569-582 (2007)).

In a reporter according to the invention the first fragment and the second fragment preferably are derived from a luciferase protein. Accordingly, in one embodiment, the receptor according to the invention is a fused protein comprising a first luciferase fragment, a second luciferase fragment and a protein kinase sequence section, wherein the first and the second luciferase fragments are derived from different sections of the same luciferase, and wherein the protein kinase sequence section intervenes between the first fragment and the second fragment.

The term "luciferase fragment" refers to a protein fragment, wherein the sequence of this fragment is derived from a section of full-length luciferase protein. The first and the second luciferase fragments are derived from two different sections of the same full-length luciferase protein. Depending on the fragmentation point, their amino acid sequence may be of different size/length. The *Renilla* luciferase fragments, i.e. derived from a *Renilla* luciferase (Rluc) sequence, turned out to be valuable reporter protein fragments. In addition to Rluc other luciferases may be used to generate a functional kinase reporter platform according to the invention. Any luciferase based PCA reporter enzyme might be applicable to generate a kinase reporter according to the invention. Preferably the luciferase fragments are derived from a luciferase selected out of the group consisting of *Renilla* luciferase, *Gaussia* luciferase, firefly luciferase, and artificial systems such as NanoLuc, NanoBit, ReBiL (recombinase enhanced bimolecular luciferase). The optimization of Rluc fragmentation point for another PCA assay has been described before. It is preferred that the fragmentation of the *Renilla luciferase* sequence applies after residue 110 (Stefan, E et al., *Proc Natl Acad Sci USA*. 43, 16916-16921 (2007)). The fragments are derived from the N-terminal residues 3 to 110 or the C-terminal residues 111 to 311 of the sequence of native luciferase from *Renilla reniformis*, respectively. SEQ ID No: 17 comprises a 109 residue beginning with an additional alanine residue located N-terminally and SEQ ID No: 18 comprises a 201 residues sequence from the C-terminal part. Additionally, a similar BRAF-V600E reporter with *Gaussia* luciferase could be provided to analyze drug induced conformational rearrangements of BRAF-V600E. The *Gaussia* luciferase fragments (SEQ ID No: 19 and SEQ ID No: 20) are derived from the very small *Gaussia* luciferase (Gluc) originally secreted by the copepod *Gaussia princeps*. The fragmentation and application of Gluc in PCA was described before (Remy I, Michnick SW. A highly sensitive protein-protein interaction assay based on *Gaussia* luciferase. *Nat Meth*. 12 977-9 (2006)).

In a preferred embodiment, the reporter construct is characterized in that the luciferase fragments are derived from *Renilla* luciferase or *Gaussia* luciferase. More preferably, the first luciferase fragment has a sequence identity of at least 95%, preferably at least 98%. to SEQ ID No: 17 or 19 and the second luciferase fragment has a sequence identity of at least 95%, preferably at least 98%, to SEQ ID No: 18 or 20. Mutations in the native sequence of Rluc may be tolerated or even beneficial for bioluminescence activity of the reassembling fragments. Thus, 95% sequence identities with the native Rluc or Gluc sequence are sufficient for the fragments.

Generally, the location of the first fragment and the second fragment within the reporter is open. Two alternative variants may be conceived: for the arrangement of the fragment of the N-terminal part may be located i) N-terminally to the protein kinase sequence section or ii) C-terminally to the protein kinase sequence section, with the C-terminal fragment being located at the other side, respectively. However, it is preferred that the first luciferase fragment having a sequence identity of at least 95% to SEQ ID No: 17 or 19 is located N-terminally to the kinase protein and the second luciferase fragment having a sequence identity of at least 95% to SEQ ID No: 18 or 20 is coupled C-terminally to the kinase protein. More generally, it may be preferred that the first fragment is derived from an N-terminal section of a split protein and within the reporter said first fragment is located N-terminally to the protein kinase sequence section and that the second fragment is derived from a C-terminal section of a split protein and within the reporter said second fragment is located C-terminally to the protein kinase sequence section.

The reporter according to the invention is constructed to comprise an N-terminal sequence section comprising a fragment, a kinase sequence and a C-terminal section comprising another fragment. Additionally, the reporter may preferably comprise one or two linker sequence(s) intervening between the N-terminal fragment and the protein kinase sequence section and/or between the protein kinase sequence section and the C-terminal fragment. Preferably, two linkers enclose the protein kinase sequence section; e.g. the reporter comprises two interjacent 10-aa linkers $(GGGGS)_2$. Preferably linker sequence(s) consist(s) of small and flexible residues such as glycine and/or serine residues. Linker sequences may consist of for example 5 to 50, 5 to 20, 8 to 16 or 10 to 12 residues. A linker sequence may for example be GGGGSGGGGS (SEQ ID No: 21) or similar flexible regions of amino acids with no or small side chains.

In a preferred embodiment of the invention with one or two linker(s), the linker(s) is/are glycine rich linker(s), preferably the linker(s) has/have a sequence according to SEQ ID No: 21.

Thus, in specific embodiments the reporter has a protein sequence with at least 95%, preferably at least 98% sequence identity to a protein sequence selected out of the group consisting of SEQ ID No: 22 to 24. Those exemplary reporters comprise the wild-type sequence of BRAF or MEK1. Respective mutated variants, i.e. with one, two or three single point mutations in the kinase sequence section can be obtained by sited directed mutagenesis as shown in the examples.

In another aspect, the present invention relates to a polynucleotide encoding for a reporter according to the invention.

The term "polynucleotide" is to be understood synonymous to oligonucleotide and denotes nucleic acid single-stranded and double-stranded polymers of nucleotide monomers, including 2'-deoxyribonucleotides (DNA) and ribonucleotides (RNA). The person skilled in the art may derive the respective RNA or DNA sequence easily from the protein reporter sequence. The general approach for generating a polynucleotide with a luciferase fragment for a PCA assay was described previously (Stefan, E. et al. Quantification of dynamic protein complexes using *Renilla* luciferase fragment complementation applied to protein kinase A activities in vivo. *Proc Natl Acad Sci USA* 104, 16916-21 (2007)). In one embodiment the polynucleotide may be a plasmid comprising a DNA sequence section encoding for the reporter. It may be preferred that the plasmid further contains suitable sequence section(s) for expression in eukaryote cells and/or for selection of cells. Such a plasmid is useful as vector for generating a cell expressing the reporter according to the invention.

Moreover, the invention provides a cell comprising a polynucleotide according to the invention, said cell expressing a reporter according to the invention.

Thus, a cell according to invention is capable of expressing the engineered reporter according to the invention. Such a cell or cell line according to the invention is useful for studying and quantifying the influence of mutations and exogenous factors such as drugs on the kinase activity and the intramolecular conformation of the kinase. The polynucleotides may be transfected to any modified cancer cell line. In one embodiment the cell line may be a melanoma cell line. An exemplary procedure for obtaining a cell according to the invention is given in the detailed description. For example, the cell according to the invention may be derived from an established cell line such as a cell line selected out of the group comprising HEK293, SW480 and U2OS.

Finally, the invention relates to a method for measuring an intramolecular interaction within a protein kinase reporter with a protein fragment complementation assay comprising the steps of a) providing a reporter according to the invention b) providing conditions suitable for detecting a signal from the split protein, wherein said signal indicates assembling of the first fragment and second fragment upon an intramolecular interaction within the reporter.

The method includes the essential steps for a PCA assay, which allow to detect the conformation/activities of a reporter with a specific protein kinase sequence section. Thus, it is suitable to study the influence of mutations in a kinase sequence and drug interaction with consequences on kinase conformations/activities. Preferably, the method is performed as a cell based method, wherein the reporter is expressed in an engineered cell. Suitable cells have been described before and examples of the cell-based assay are illustrated below. While a cell-based assay may be preferred, the method can also be conducted in an embodiment without cells, e.g. the reporter is provided in an isolated form. The reporter might be generated in vitro, excreted from cells or obtained by breaking up cells and using the lysate.

Suitable conditions for step b) depend on the fragments and the split protein from which the fragments are derived. Detecting a signal may also refer to detecting viability of cells expressing the reporter under specific conditions (i.e. clonal selection). Preferably, the split protein itself or its catalytic activity is detectable with a non-invasive read-out technique in a cellular context, e.g. colorimetric or fluorometric. In some embodiments it may be necessary to provide a substrate of the split protein to detect a signal associated with reassembly of the split protein via its catalytic activity.

In a preferred embodiment, the fragments in the protein kinase reporter are derived from a luciferase and step b) includes providing a bioluminescence substrate and detecting bioluminescence, wherein a bioluminescence signal indicates that the luciferase fragments assemble to exhibit a luciferase activity. Thus, the bioluminescence signal depends on the intramolecular interaction within the reporter.

The term "luciferase substrate" refers to so called luciferins, which are compounds that are oxidized by an active luciferase to form a light emitting molecule. The luciferase substrate provided in the method (step b) may be for example selected out of the chemical group of coelenterazine compounds, which are also referred to as CTZ or CLZN. Suitable examples may be benzylcoelenterazine (also known as coelenterazine h, 2,8-dibenzyl-6-(4-hydroxyphenyl)imidazo[1,2-a]pyrazin-3(7H)-one, CAS: 50909-86-9). This substrate of *Renilla* luciferase (Rluc) may be preferred in combination with constructs comprising SEQ ID No: 17 and 18. Alternatively, native coelenterazine may be used (6-(4-hydroxyphenyl)-2-[(4-hydroxyphenyl)methyl]-8-(phenylmethyl)-7H-imidazo[3,2-a]pyrazin-3-one, CAS: 55779-48-1). Coelenterazine is a substrate for a *Gaussia* luciferase (Gluc) and may be preferred in combination with constructs comprising SEQ ID No: 19 and 20. Other luciferins from the coelenterazine class useful according to the invention include e.g. Coelenterazine 400a (Bis-deoxycoelenterazine, 2,8-dibenzyl-6-phenyl-imidazo[1,2A] pyrazin-3-(7H)-1, CAS 70217-82-2), e-Coelenterazine (Coelenterazine-E, Benz[f]imidazol[1,2-a]quinoxalin-3 (6H)-one,5,11-dihydro-8-hydroxy-2-[(4-hydroxyphenyl-methyl]-12-(phenylmethyl), CAS: 114496-02-5), Coelenterazine-Fluoride (Coelenterazine F, 8-benzyl-2-(4-fluorobenzyl)-6-(4-hydroxyphenyl)imidazo[1,2-a]pyrazin-3 (7H)-one, CAS: 123437-16-1), e-Coelenterazine-F(Benz[f] imidazol[1,2-a]quinoxalin-3 (6H)-one,5,11-dihydro-8-hydroxy-2-[(4-fluorophenyl-methyl]-12-(phenylmethyl)), v-Coelenterazine (Coelenterazine-v, 16-benzyl-5-hydroxy-13-[(4-hydroxyphenyl)methyl]-11,14,17-triazatetracyclo [8.7.0.0^{2,7}.0^{11,15}]heptadeca-1(10),2(7),3,5,8,13,15-heptaen-12-one), Coelenterazine hcp (2-benzyl-8-(cyclopentylmethyl)-6-(4-hydroxyphenyl)imidazo[1,2-a] pyrazin-3 (7H)-one CAS: 123437-32-1), Coelenterazine cp (8-(cyclopentylmethyl)-2-(4-hydroxybenzyl)-6-(4-hydroxyphenyl)imidazo[1,2-a]pyrazin-3 (7H)-one, CAS: 123437-25-2), Coelenterazine fcp (8-(cyclopentylmethyl)-2-(4-fluorobenzyl)-6-(4-hydroxyphenyl)imidazo[1,2-a]pyrazin-3 (7H)-one CAS: 123437-33-2), Coelenterazine ip (8-(isopropylmethyl)-2-(4-hydroxybenzyl)-6-(4-hydroxyphenyl)imidazo[1,2-a]pyrazin-3 (7H)-one). These compounds may be suitable in a method according to the invention as long as they are substrate of the intact luciferase formed by the fragments. A person skilled in the art can easily verify a substrate as suitable with the respective full-length luciferase.

The method is also applicable to study the effect of exogenous factors on the intramolecular interaction of a kinase. Thus, the method may be for example used to investigate a candidate compound. A "candidate compound"

could be any (macro) molecule for which it is of interest to study the influence on the kinase conformation/activity. Thus, the method may be applied to screen for compounds influencing the conformation/activity. In such situation the candidate compound may be any compound, preferably a small organic molecule. Alternatively, the compound may be a compound which is known to be a kinase inhibitor, e.g. a kinase inhibitor known to be specific for constitutively active kinases, such as a kinase inhibitor for carcinogenic mutants of a RAF kinase, such as vemurafenib, PLX8394, dabrafenib, and encorafenib. The method according to the invention indicated the specificity of these BRAF inhibitors (BRAFi) as the bioluminescence of the wild type reporter was unaffected. Moreover, the signal was not sensitive to inhibitors of other kinases. Thus, the assay provides a method for identifying and characterizing kinase inhibitors specific for a distinct kinase sequence. In a similar way also the impact of both ATP-competitive and allosteric inhibitors on the RAF/MEK conformation can be studied.

In this embodiment the method is conducted in presence of the candidate compound and the effect of the candidate compound on the interaction is determined by comparing the signal as detected in presence of the candidate compound versus the signal in absence of the candidate compound. Preferably, the candidate compound is added before the conditions suitable for detecting a signal are provided (before step b). For example, the candidate compound is added, e.g. several minutes, several hours, such as 1 to 3 hours, but also days before addition of a substrate of the split protein such as a luciferase substrate in case of a reporter with luciferase fragments.

DETAILED DESCRIPTION OF THE INVENTION

The invention will now be described in more detail by the following figures and non-limiting examples.

The figures show:

FIG. 1: Intramolecular RAF kinase PCA reporter. Schematic depiction of the RAF reporter for intramolecular Rluc PCA. Defined cancer mutations or drugs shift the reporter either to an open or closed conformation resulting in a decrease or an increase of Rluc PCA emitted bioluminescence respectively.

Figure 2:
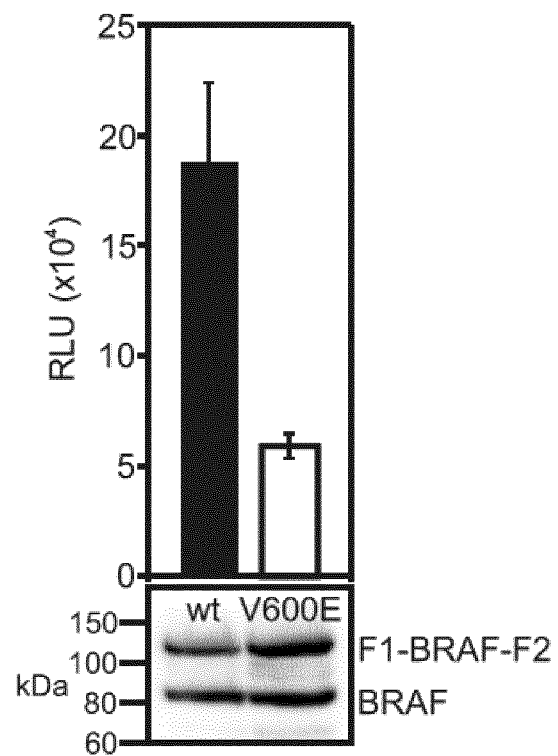

FIG. 2: Measurements of RAF Rluc PCA reporter signals. BRAF Rluc PCA fragment F[1] and F[2]complementation was measured using transiently transfected HEK293 cells. Immunoblotting shows expression levels of endogenous BRAF and overexpressed F1-BRAF-F2 and F1-BRAF (V600E)-F2 in HEK293 cells 48 h post transfection.

Figure 3:
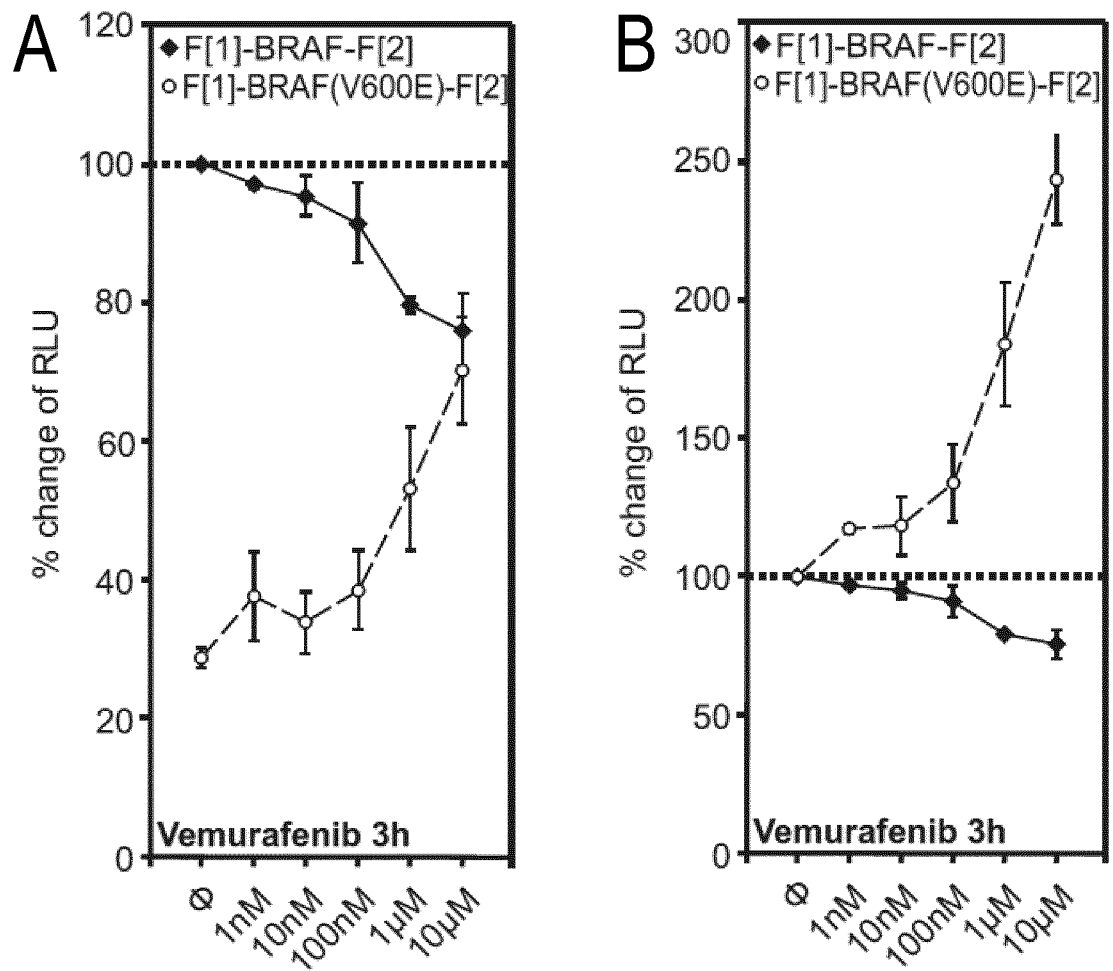

FIG. 3: Dose-dependent recordings of RAF reporter signals and cancer drug interactions. Dose-dependent effect of the BRAFi vemurafenib on the conformation of BRAF and BRAF-V600E PCA reporter (SEM from n=4 independent experiments; 3 h treatments). FIG. 3A shows the relative change in respect to the initial luciferase signal of the wild type reporter. In FIG. 3B, the same data is presented and the results for the individual reporters have been normalized to the respective signal of the untreated reporter.

Figure 4:
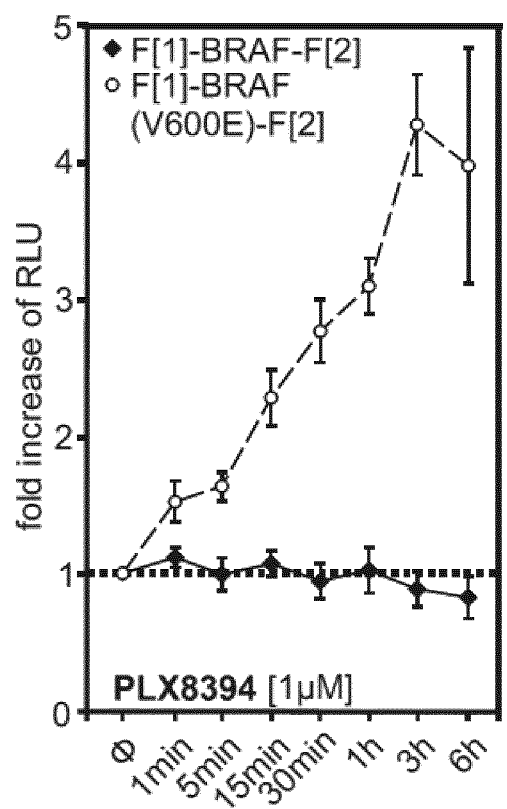

FIG. 4: Time-dependent recordings of RAF reporter signals and BRAFi interactions. Time-dependent impact of BRAFi PLX8394 (1 µM) on the BRAF and BRAF-V600E reporter conformation measured using transiently transfected HEK293 cells.

Figure 5:
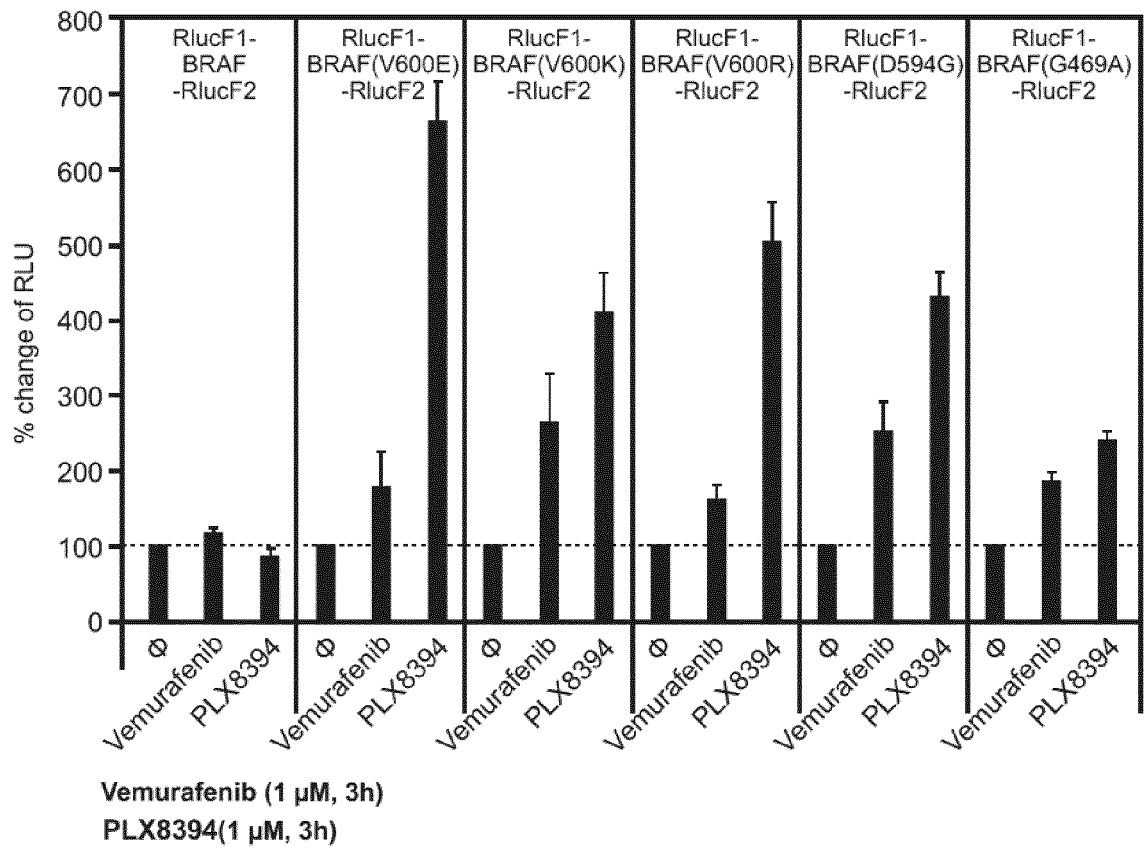

FIG. 5: Measurements of RAF reporter signals and BRAFi interactions. BRAF Rluc PCA fragment F[1] and F[2]complementation using the wild type reporter and the mutant intramolecular BRAF PCA reporter (V600E, V600K, V600R, D594G, G469A) was measured using transiently transfected HEK293 cells. The BRAFi vemurafenib and PLX8394 were used (1 µM, 3 h treatments).

Figure 6:
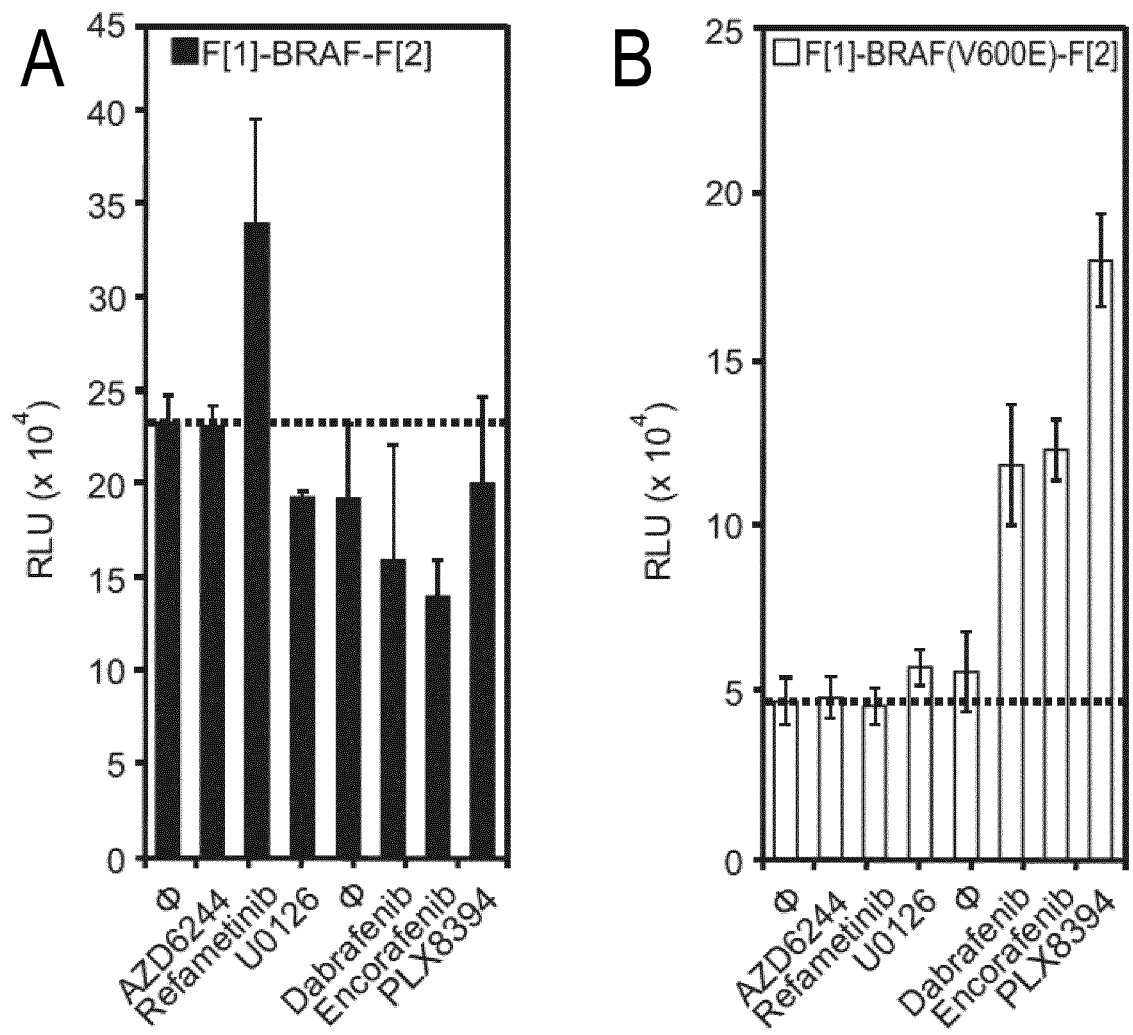

FIG. 6: Measurements of RAF reporter signals and cancer drug interactions. BRAF Rluc PCA fragment F[1] and F[2]complementation using the wild type reporter (FIG. 6A) and the mutant intramolecular BRAF PCA reporter (V600E) (FIG. 6B) was measured using transiently transfected HEK293 cells. The MEK1/2 inhibitors AZD6244, refametinib, and U0126 (1 µM, 3 h treatments) and the BRAFi dabrafenib, encorafenib and PLX8394 (1 µM, 3 h treatments) were used.

Figure 7:
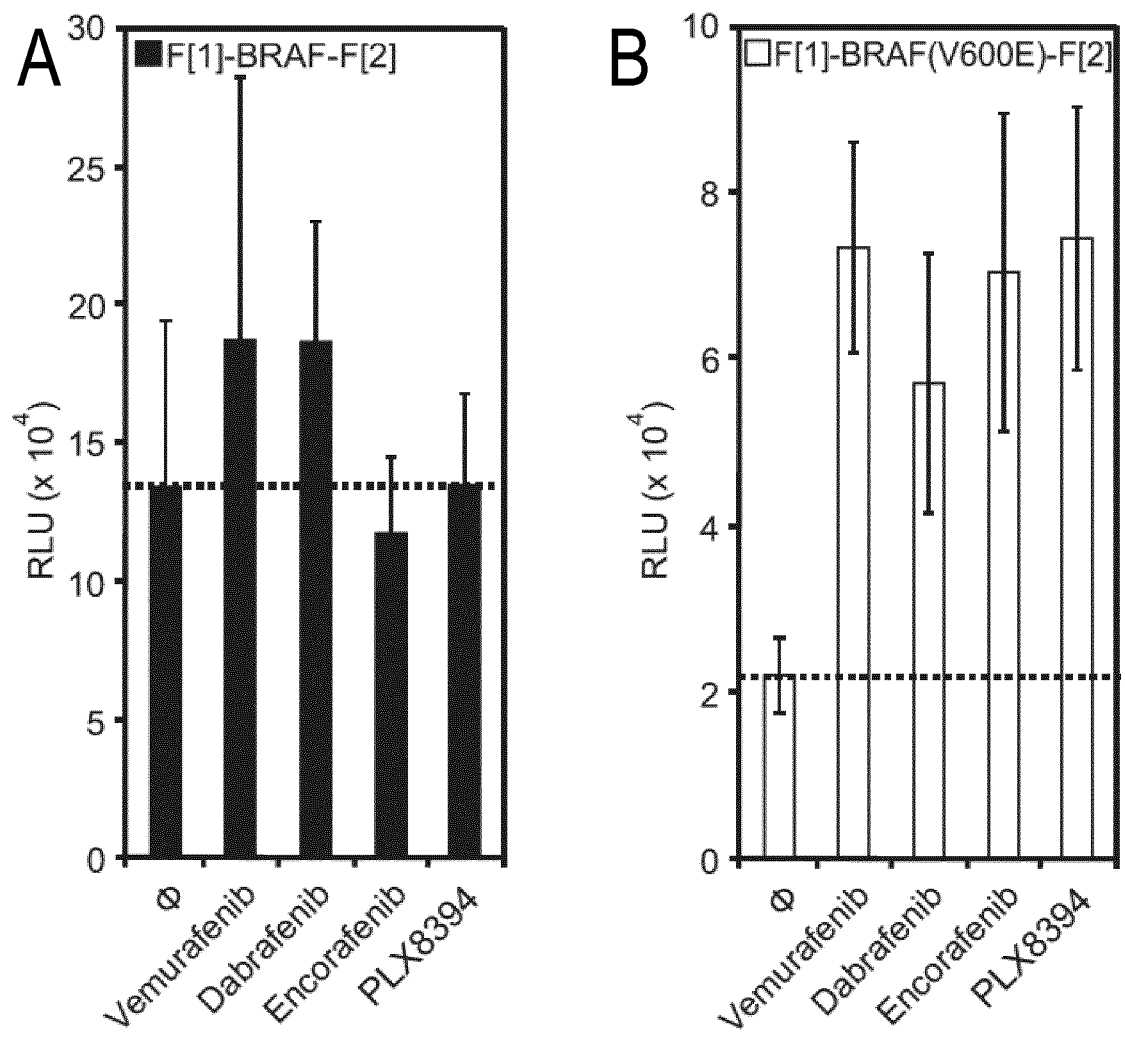

FIG. 7: Measurements of RAF reporter signals and cancer drug interactions in stable reporter cell lines. BRAF Rluc PCA fragment F[1] and F[2]complementation using the wild type reporter (FIG. 7a) and the mutant intramolecular BRAF PCA reporter (V600E) (FIG. 7B) was measured using stable SW480 cell lines. The BRAFi vemurafenib, dabrafenib, encorafenib and PLX8394 (1 µM, 3 h treatments) were used.

Figure 8:
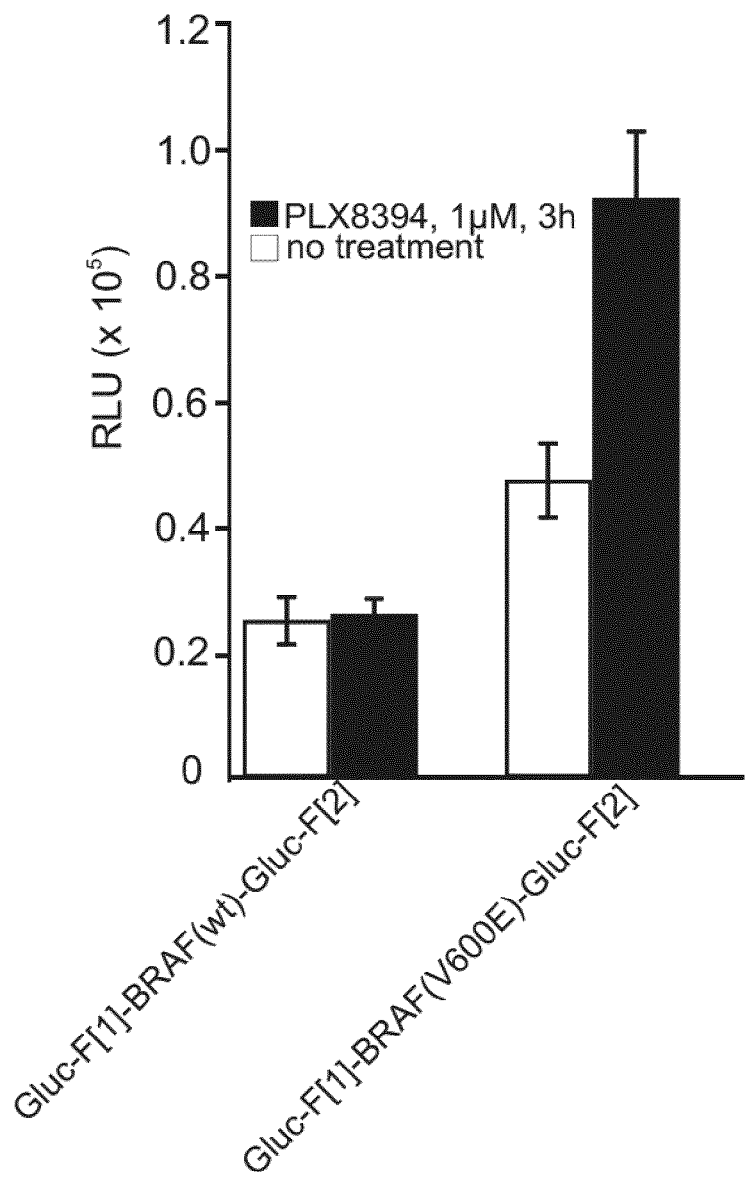

FIG. 8: Measurements of RAF Gluc PCA reporter signals and BRAFi interactions. BRAF Gluc PCA fragment F[1] and F[2]complementation using the wild type reporter and the mutant BRAF PCA reporter (V600E) was measured using transiently transfected HEK293 cells. The BRAFi PLX8394 was used (1 µM, 3 h treatments).

Figure 9:
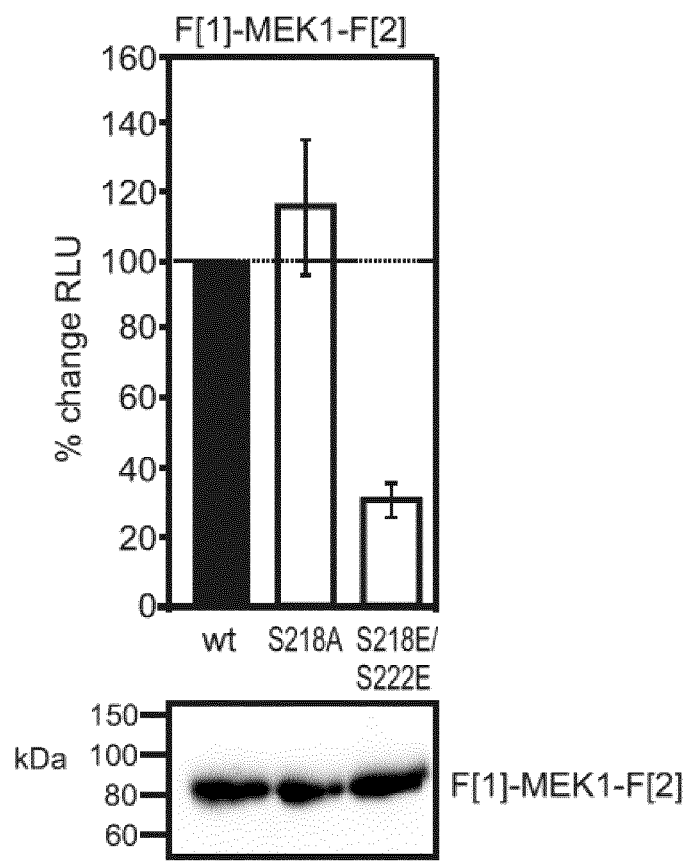

FIG. 9: Measurements of MEK1 reporter signals. MEK1 Rluc PCA fragment F[1] and F[2]complementation using the wild type reporter, the inactive (phosphorylation deficient; S218A) and active (phospho-mimetic kinase status; S218E, S222E) MEK1 PCA reporter was measured using transiently transfected HEK293 cells. Immunoblotting confirms equal levels of reporter expression.

Figure 10:
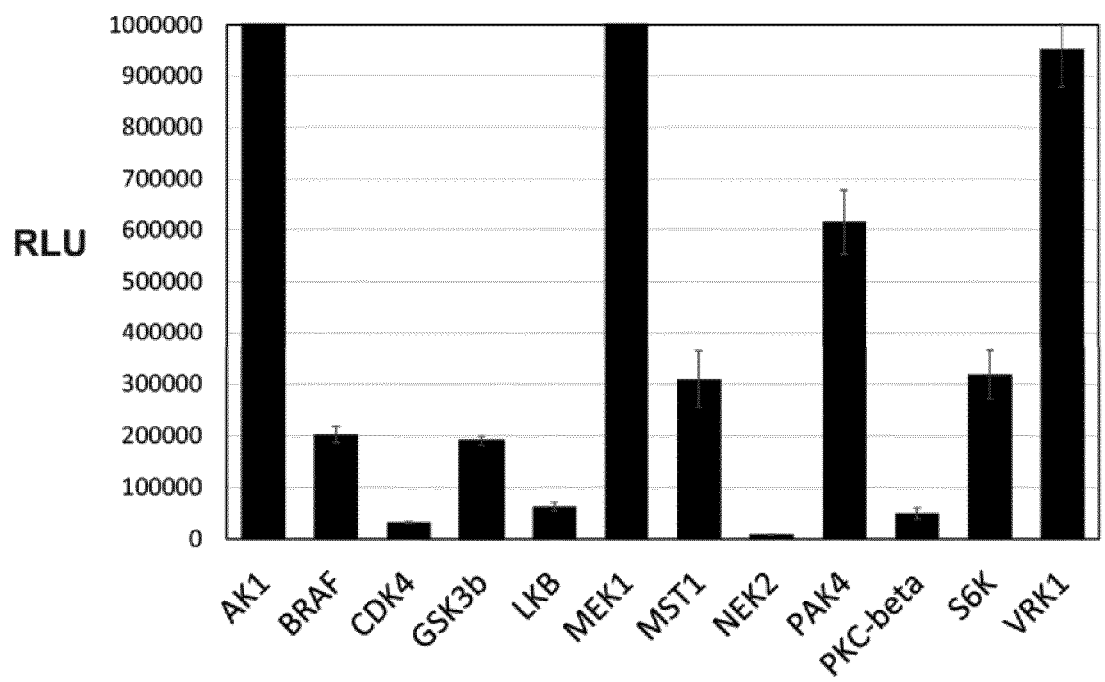

FIG. 10: Measurements of PCA reporter signals for various kinase reporters. For each of the indicated kinases Rluc PCA fragment F[1] and F[2]complementation was measured using HEK293 cells transiently expressing the construct for the respective kinase, wherein the signal of the MEK1 reporter is given for comparison. Explanations for the abbreviations indicating the specific kinase are given in Table 1 below.

Example 1: RAF and MEK Reporters

Method
Cell Culture and Antibodies.

HEK293 and SW480 cells were grown in DMEM supplemented with 10% (vol/vol) FBS. Cells were passaged three times a week to keep the cells in culture. Transient transfections were performed with Transfectin reagent (Bio-Rad, #1703350). Cells were treated with the RAF inhibitors PLX4032 (Vemurafenib; Medchem Express, #HY-12057), LGX818 (Encorafenib; Medchem Express, #HY-15605), GSK2118436A (Dabrafenib; Selleckchem, #S2807) or PLX8394 (Medkoo biosciences, #206168) and the MEK inhibitors U0126 (Selleckchem, #S1102), AZD6244 (Selumetinib) or BAY86-9766 (Refametinib) with indicated concentrations and for the indicated time frames. The primary antibody used was anti-BRAF(F-7) (Santa Cruz Biotechnology, #sc-5284).

Expression Constructs.

The Rluc PCA hybrid proteins F[1]-BRAF-F[2] and F[1]-BRAF(V600E)-F[2] have been generated using the identical cloning approach. Following PCR amplification of the human BRAF or BRAF(V600E) gene, the coding region of the BRAF protein (SEQ ID No: 2 or 5) was fused N-terminally with F[1](SEQ ID No: 13) and C-terminally with F[2](SEQ ID No: 17) of the Rluc PCA coding region. In addition. the sequence of two interjacent 10-aa linkers (GGGGS)$_2$ (SEQ ID No: 18) was integrated by cloning. As vector backbone we used the pcDNA3.1 plasmid. The MEK1 expression constructs (s. SEQ ID No: 23) and the Gluc PCA based BRAF reporter (s. SEQ ID No: 24) were prepared analogously.

Mutagenesis.

Site directed mutagenesis have been performed to generate following mutations in the reporter constructs: V600E, V600K, V600R, D594G, and G469A in BRAF and S218A and the S218E/S222E double mutation in MEK1.

Renilla/Gaussia Luciferase PCA Experiments.

Cells were grown in DMEM supplemented with 10% FBS. Indicated versions of the Rluc PCA based biosensor were transiently overexpressed in 24-well plate format. 48 hours post-transfection, the growth medium was partially removed and different compounds added with concentrations as indicated in the figure legends. To measure the dose-dependent effect of the lead molecules (candidate compounds) on the intramolecular Rluc PCA reporter, the attached cells were treated with different concentrations and for different time-frames. The time-dependent consequences of the lead compounds on kinase conformations were recorded with a final compound concentration of 1 µM. For the Rluc PCA measurements the growth medium was carefully removed and the cells were washed with PBS. Cells were resuspended in PBS and the cell suspensions were transferred to 96-well plates and subjected to luminescence analysis using the LMax™-II-384 luminometer (Molecular Devices). Rluc luminescence signals were integrated for 10 seconds with a delay time of 3 seconds following addition of 20 µl of the Rluc substrate benzyl-coelenterazine (5 µM; Nanolight, #301) in PBS with a concentration of 25 nM. Dose-dependent effects of drug exposure on luminescence signals originating from BRAF conformations were compared using indicated controls. Cells were collected after PCA measurements and lysed with Laemmli sample buffer to control the protein expression levels. In case of Gluc reporters, coelenterazine was used as luminescence substrate.

Stable Cell Lines.

SW480 cells were grown in DMEM supplemented with 10% FBS. Transient transfection was performed with Transfectin reagent (Bio-Rad, #1703350). 48 h post transfection the growth media was exchanged and 25 µl Zeocin (Invitrogen, #R25001) was added as selection marker for the pcDNA3.1 construct with a final concentration of 250 µg/ml. The growth media supplemented with Zeocin was exchanged every day for 5 days. Stable clones with a diameter of ~1 mm were selected and transferred to 24-well plates. They were grown to confluency and transferred to 12-well plates. 0.5×10$^6$ cells of each clone were selected for Rluc PCA measurement to compare expression levels of the BRAF reporters. The well attached SW480 cells have been subjected to Rluc PCA measurements.

Results

As starting point, a protein-fragment complementation assay (PCA) was analyzed with reporters consisting of fused full length BRAF and BRAF-V600E sequences with fragment 1 and 2 (F[1] and FM) of the Renilla luciferase (Rluc). Following transient expression of BRAF and BRAF-V600E reporter in HEK293 cells, a significantly elevated bioluminescence signals was observed with wild type BRAF compared to the open conformation engaging the BRAF-V600E reporter (FIG. 2). It is believed that the amino acid exchange V600E serves as phospho-mimetic substitution in the BRAF kinase domain which creates a catalytically active BRAF (open conformation) representing one of the most recurrent oncogenic human disease mutations.

To demonstrate the general utility of the intramolecular Rluc PCA reporter method to profile RAF: drug interactions, a collection of structurally diverse BRAF inhibitors (BRAFi), vemurafenib, PLX8394, dabrafenib, and encorafenib respectively was investigated. Vemurafenib, one of the V600E selective inhibitors, showed a dose-dependent shift to the closed kinase conformation exclusively with the V600E mutant reporter. The wild type BRAF complex was marginally affected showing a slightly reduced luciferase signal following increased drug dose exposure (FIG. 3). The data of the BRAF complementation assay is presented in two modes: In the left panel the relative change to the initial luciferase signal is indicated (FIG. 3A); in the right panel the untreated reporter signal has been set to 100% (FIG. 3B). The vemurafenib-dependent change of the conformation is evident in both panels.

Next, the intramolecular BRAF PCA reporter was subjected to kinase inhibitor PLX8394 to study the time dependent effects on BRAF-V600E. An immediate shift of the BRAF-V600E reporter to the closed conformation was observed increasing up to 3 h. The wild type BRAF reporter was not affected (FIG. 4). This result underlines the selective binding of PLX8394 to BRAF-V600E shifting it to the inactive and closed kinase conformation.

Additionally, a collection of different BRAF reporters was generated comprising four different BRAF patient mutations, V600K, V600R, D594G, and G469A respectively. Wild type and the mutant intramolecular BRAF PCA reporters (V600E, V600K, V600R, D594G, G469A) were subjected to time dependent treatments with the BRAFi vemurafenib and PLX8394. With all mutant reporters, a significant shift to the closed conformation triggered by the investigated compound was observed as indicated by the increase of the bioluminescence signal of the intramolecular PCA reporter (FIG. 5B). The wild type reporter signal was not susceptible to the presence of these inhibitors (FIG. 5A).

To determine drug specificity, other lead molecules were integrated to underline the specificity of the tested BRAFi and the sensitivity of the reporter. The reporters were expressed in HEK293 cells and the cells treated with 1 µM of the MEK1/2 inhibitors AZD6244, refametinib, and U0126 (Caunt, C. J. et al. MEK1 and MEK2 inhibitors and cancer therapy: the long and winding road. Nat Rev Cancer 10, 577-592 (2015)) for 3 h in parallel to the treatments with the BRAFi dabrafenib, encorafenib and PLX8394. The wild type reporter showed only slight changes in the luminescence signal (FIG. 6A). However, the signal of the BRAF reporter V600E was exclusively influenced by the BRAF specific inhibitors and showed a shift to the closed conformation (FIG. 6B).

To determine whether this kinase reporter can be used in a different cell settings, stable colon cancer SW480 cell lines were generated expressing either wild type or the V600E BRAF kinase reporter. These cells showed similar reactions upon exposition to the tested BRAFi: Only the bioluminescence signal of the BRAF mutant V600E reporter increased indicating the shift to the closed kinase conformation (FIG. 7).

To demonstrate that other luciferase based PCA reporter can be adapted for the profiling of BRAF: drug interactions intramolecular PCA reporters based on Gaussia luciferase (Gluc) were generated: GlucF[1]-BRAF-GlucF[2] and GlucF[1]-BRAF-V600E-GlucF[2]. Following transient expression in HEK293 for 48h, a significant luciferase signal was observed for both hybrid constructs. Subsequent to 3h treatments with PLX8394 enhanced the luciferase signal exclusively with the V600E BRAF mutant. PLX8394, one of the V600E selective inhibitors, showed a dose-dependent shift to the closed kinase conformation exclusively with the BRAF-V600E mutant reporter. The wild type BRAF complex was not affected (FIG. 8). Thus, the concept is not limited to Rluc reporters and other PCA fragments can be integrated into the reporter platform suitable for measuring intramolecular kinase rearrangements.

Next, a MEK1 reporter for the intramolecular PCA analyses with Rluc fragments was investigated. Amongst other kinases active RAF kinases directly phosphorylate MEK1 or MEK2 at position S218 and S222. Phosphorylation of MEK by RAF converts it into the active open conformation. Interestingly, compared to RAF the MEK kinases are much smaller but nevertheless they contain a N-terminal negative regulatory region (=autoinhibitory domain). The wild type version RlucF[1]-MEK1-RlucF[2], an inactive mutant reporter RlucF[1]-MEK1(S218A)-RlucF[2] and an active conformation reporter RlucF[1]-MEK1(S218E,S222E)-RlucF[2], were generated. Following transient expression in HEK293 for 48h, significant luciferase signals were observed for all three hybrid constructs. Interestingly, the phosphorylation mimetic RlucF[1]-MEK1(S218E,S222E)-RlucF[2]PCA reporter showed a significantly reduced luciferase signal indicating a shift to the open MEK1 kinase conformation (FIG. 9). The results from the MEK reporters support that the MEK activation by RAF-phosphorylation relieves the auto-inhibition, wherein the auto-inhibition mechanism is based on an intramolecular interaction between the kinase domain and the N-terminal regulatory region. The data underline that besides RAF also other kinases containing a regulatory sequence, e.g. a regulatory N-terminal to the kinase domain, exhibit open and closed enzyme conformations reflected by the difference in PCA signal.

Example 2: Further Kinase Reporters

Method

In analogy, to the previous experiments other ten kinases were investigated. The intramolecular PCA constructs were designed with a C-terminal Rluc fragment [1], a first linker, the full-length sequence of the kinase of interest, a second linker, and an N-terminal Rluc fragment [2]. The constructs were expressed in HEK293 cells. Rluc fragment complementation was monitored by measurement of the relative luminescence in presence of the Rluc substrate benzyl-coelenterazine. The conditions for the experiments were selected as described above and the RLU signal for the MEK1 construct is included for comparative reason.

The investigated kinases are summarized in Table 1 including the so-called uniprot ID. The latter allows to unequivocally identify the kinase on the online platform UniProt providing a database summarizing functional as well as sequence information on proteins.

TABLE 1

| Abbreviation | Descriptive name | Uniprot ID | SEQ ID |
| --- | --- | --- | --- |
| AK1 | adenylate kinase isoenzyme 1 | P00568 | 25 |
| CDK4 | Cyclin dependent kinase 4 | P11802 | 26 |
| GSK3b | Glycogen synthase kinase 3 beta | P49841 | 27 |
| LKB | Liver kinase B1; Serine/threonine kinase 11 | Q15831 | 28 |
| MEK1 | mitogen-activated protein kinase kinase | Q02750 | 13 |
| MST1 | Serine/threonine-protein kinase 4 | Q13043 | 29 |
| NEK2 | serine/threonine-protein kinase Nek2 | P51955 | 30 |
| PAK4 | p21-activated kinase 4 | O96013 | 31 |
| PKC-beta | protein kinase C beta | P05771 | 32 |
| S6K | Ribosomal protein S6 kinase | P23443 | 33 |
| VRK1 | Vaccinia-related kinase 1 | Q99986 | 34 |

Results

The selected kinases were tagged C- and N-terminally with Rluc PCA fragments (similar to the BRAF or MEK1 reporters described above). The reporters gave significant bioluminescent signals reflecting quantifiable full-length kinase conformations under basal cell conditions (FIG. 10). It will be acknowledged that these proof-of-principle experiments underline that the concept of providing an intramolecular kinase reporter is valid for those kinases, whereas the individual conditions for each kinase should be optimized.

Even under standard conditions, it will be appreciated that these reporters have the potential to be used for studying intermolecular interactions with small molecules, substrates, and multivalent interaction partners (competitive and allosteric binders). These data underline that also further kinases of the kinome are accessible for reporters according to the present invention.

The invention claimed is:

1. A reporter for a protein fragment complementation assay: wherein the reporter is a single fused protein comprising a first fragment, a second fragment, and a protein kinase sequence section, wherein the first fragment and the second fragment are derived from different sections of the same split protein, wherein the protein kinase sequence section intervenes between the first fragment and the second fragment, and wherein the protein kinase sequence section comprises a kinase domain sequence and one or more regulatory sequences, and wherein the protein kinase sequence section is selected from the group consisting of rapidly accelerated fibrosarcoma (RAF) protein sequence and MAPK/ERK kinase (MEK) protein sequence.

2. The reporter of claim 1, wherein the protein kinase sequence section is a RAF protein sequence, wherein the RAF protein sequence has a sequence identity of at least 95% to a sequence selected from the group consisting of SEQ ID No: 1 to SEQ ID No: 3.

3. The reporter of claim 1, wherein the protein kinase sequence section is a MEK protein sequence, wherein the MEK protein sequence has a sequence identity of at least 95% to a sequence selected from the group consisting of SEQ ID No: 13 and SEQ ID No: 14.

4. The reporter of claim 1, wherein the first fragment and the second fragment are derived from a luciferase.

5. The reporter of claim 1, wherein the first fragment is derived from an N-terminal section of a split protein and within the reporter said first fragment is located N-terminally to the protein kinase sequence section and that the second fragment is derived from a C-terminal section of a split protein and within the reporter said second fragment is located C-terminally to the protein kinase sequence section.

6. The reporter of claim 1, wherein the fused protein comprises one or two linkers, wherein the one or two linkers intervene between the first fragment and the protein kinase sequence section and/or between the second fragment and the protein kinase sequence section.

7. The reporter of claim 6, wherein the at least one linker is a glycine rich linker.

8. The reporter of claim 1, wherein the protein kinase sequence section is a RAF protein sequence, wherein the RAF protein sequence has a sequence selected from the group consisting of SEQ ID No: 1 to SEQ ID No: 12.

9. The reporter of claim 1, wherein the protein kinase sequence section is a MEK protein sequence, wherein the MEK protein sequence has a sequence selected from the group consisting of SEQ ID No: 13 to SEQ ID No: 16.

10. The reporter of claim 1, wherein the first fragment and the second fragment are derived from a luciferase selected from Renilla luciferase and Gaussia luciferase, and where the first luciferase fragment has a sequence identity of at least 95% to SEQ ID No: 17 or SEQ ID No: 19 and the second luciferase fragment has a sequence identity of at least 95% to SEQ ID No: 18 or SEQ ID No: 20.

11. The reporter of claim 6, wherein the glycine rich linker has a sequence of SEQ ID No: 21.

12. The reporter of claim 8, wherein the RAF protein sequence has a sequence selected from the group consisting of SEQ ID No: 2, SEQ ID No: 5, SEQ ID No: 6, SEQ ID No: 7, SEQ ID No: 8, and SEQ ID No: 9.

13. The reporter of claim 9, wherein the MEK protein sequence has a sequence selected from the group consisting of SEQ ID No: 13 and SEQ ID No: 16.

14. A method for measuring an intramolecular interaction within a protein kinase reporter in a protein fragment complementation assay comprising the steps of a) providing the reporter of claim 1; and
   b) providing conditions suitable for detecting a signal from the split protein, wherein said signal indicates assembling of the first fragment and the second fragment upon an intramolecular interaction within the reporter.

15. The method of claim 14,
   wherein the first fragment and the second fragment of the reporter provided in step a) are derived from a luciferase and wherein the conditions of step b) include
      providing a bioluminescence substrate for the luciferase, and
      detecting bioluminescence, wherein said bioluminescence indicates reassembling of the first luciferase fragment and the second luciferase fragment upon the intramolecular interaction within the reporter.

16. The method of claim 15, wherein the bioluminescence substrate is selected from the group consisting of benzylcoelenterazine, native coelenterazine, coelenterazine h, coelenterazine 400a, e-coelenterazine, coelenterazine-fluoride, e-coelenterazine-F, v-coelenterazine, coelenterazine hcp, coelenterazine cp, coelenterazine fcp, and coelenterazine ip.

17. The method of claim 14, wherein the reporter is provided within a cell comprising a polynucleotide encoding for the reporter and under conditions suitable for expression of the reporter.

18. A method for measuring an effect of a candidate compound on the intramolecular interaction within a protein kinase reporter, comprising conducting the method of claim 14 in the presence of the candidate compound and determining the effect of the candidate compound on the intramolecular interaction by comparing a first signal as detected in the presence of the candidate compound versus a second signal as detected in the absence of the candidate compound.

* * * * *